(12) United States Patent
Sim et al.

(10) Patent No.: US 8,765,749 B2
(45) Date of Patent: Jul. 1, 2014

(54) 1,6-DISUBSTITUTED INDOLE COMPOUNDS AS PROTEIN KINASE INHIBITORS

(75) Inventors: Tae Bo Sim, Seoul (KR); Young Jin Ham, Seoul (KR); Kyung Ho Yoo, Seoul (KR); Chang Hyun Oh, Seoul (KR); Jung Mi Hah, Seoul (KR); Hwan Geun Choi, Seoul (KR); Hwan Kim, Gyeonggi-do (KR); Eun Jin Jun, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 175 days.

(21) Appl. No.: 13/504,355

(22) PCT Filed: Oct. 20, 2010

(86) PCT No.: PCT/KR2010/007205
§ 371 (c)(1),
(2), (4) Date: Jul. 6, 2012

(87) PCT Pub. No.: WO2011/052923
PCT Pub. Date: May 5, 2011

(65) Prior Publication Data
US 2012/0271048 A1    Oct. 25, 2012

(30) Foreign Application Priority Data
Oct. 27, 2009 (KR) ........................ 10-2009-0102359

(51) Int. Cl.
C07D 403/04 (2006.01)
A61K 31/404 (2006.01)
C07D 403/14 (2006.01)
C07D 405/14 (2006.01)

(52) U.S. Cl.
CPC ............ C07D 403/04 (2013.01); *C07D 403/14* (2013.01); *C07D 405/14* (2013.01); *A61K 31/404* (2013.01)
USPC ........ 514/235.8; 514/256; 544/122; 544/326; 544/327

(58) Field of Classification Search
CPC .. C07D 403/04; C07D 403/14; C07D 405/14; A61K 31/404
USPC ................ 544/122, 326, 327; 514/235.8, 256
See application file for complete search history.

(56) References Cited

FOREIGN PATENT DOCUMENTS

WO    2004/080423    9/2004
WO    2008/079918    7/2008

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer, 84(10):1424-1431,2001.*
Gura et al., Systems for identifying new drugs are often faulty, Science, 278:1041-1042, 1997.*
Simone, Oncology: Introduction, Cecil Textbook of Medicine, 20th Editino, vol. 1, pp. 1004-1010, 1996.*
N.E. Sharpless et al., Nature Reviews Drug Discovery, 741-754, 742 (2006).*
A. Kamb, Nature Reviews Drug Discovery 2, 161-165 (2005).*
F. Smith, Molecular Cancer Therapeutics, 6, 428-440, 428 (2007).*
International Preliminary Report on Patentability issued May 1, 2012, in corresponding PCT Patent Application No. PCT/KR2010/007205.
G. Manning et al., "The Protein Kinase Complement of the Human Genome", Science, vol. 298, Dec. 2002, pp. 1912-1934.
Joseph Avruch et al., "Ras Activation of the Raf Kinase: Tyrosine Recruitment of MAP Kinase Cascade", The Endocrine Society, 2001, pp. 127-155.
M. Caraglia et al., "Targeting Raf-kinase: molecular rationales and translational issues", Annals of Oncology, vol. 17, Supplement 7, Jun. 2006, pp. vii124-vii127.
Anton Yuryev et al., "Isoform-Specific Localization of A-RAF in Mitochondria", Molecular and Cellular Biology, vol. 20, No. 13, Jul. 2000, pp. 4870-4878.
Nancy H. Tran et al., "B-Raf and Raf-1 Are Regulated by Distinct Autoregulatory Mechanisms", The Journal of Biological Chemistry, vol. 280, No. 16, Apr. 2005, pp. 16244-16253.
Claudia Wellbrock et al., "The Raf Proteins Take Centre Stage", Nature Reviews, Molecular Cell Biology, vol. 5, Nov. 2004, pp. 875-885.
Rama K. Jaiswal et al., "Nerve Growth Factor-mediated Activation of the Mitogen-activated Protein (MAP) Kinase Cascade Involves a Signaling Complex Containing B-Raf and HSP90", The Journal of Biological Chemistry, vol. 271, No. 39, Sep. 1996, pp. 23626-23629.
Helen Davies et al., "Mutations of the BRAF gene in human cancer", Nature, vol. 417, Jun. 2002, pp. 949-954.
David A. Tuveson et al., "BRAF as a potential therapeutic target in melanoma and other malignancies", Cancer Cell, vol. 4, Aug. 2003, pp. 95-98.
Harith Rajagopalan et al., "RAF/RAS oncogenes and mismatch-repair status", Nature, vol. 418, Aug. 2002, pp. 934.

(Continued)

*Primary Examiner* — Deepak Rao
(74) *Attorney, Agent, or Firm* — Staas & Halsey LLP

(57) ABSTRACT

Disclosed are a 1,6-substituted indole compound having a protein kinase inhibition activity, a pharmaceutically acceptable salt, and a pharmaceutical composition for prevention and treatment of cancers caused by abnormal cell growth comprising the compound as an effective ingredient.

Since the novel indole compound exhibits superior inhibition activity against various protein kinases involved in growth factor signal transduction, it is useful as an agent for preventing or treating cancers caused by abnormal cell growth.

7 Claims, 1 Drawing Sheet

(56) References Cited

OTHER PUBLICATIONS

Giuliana Salvatore et al., "Analysis of BRAF Point Mutation and RET/PTC Rearrangement Refines the Fine-Needle Aspiration Diagnosis of Papillary Thyroid Carcinoma", The Journal of Clinical Endocrinology & Metabolism, Oct. 2005—pp. 5175-5180.

Paul T.C. Wan et al., "Mechanism of Activation of the RAF-ERK Signaling Pathway by Oncogenic Mutations of B-RAF", Cell, vol. 116, Mar. 2004, pp. 855-867.

James Tsai et al., "Discovery of a selective inhibitor of oncogenic B-Raf kinase with potent antimelanoma activity", PNAS, vol. 105, No. 8, Feb. 2008, 3041-3046.

Clara Montagut et al., "Elevated CRAF as a Potential Mechanism of Acquired Resistance to BRAF Inhibition in Melanoma", Cancer Research, vol. 68, No. 12, Jun. 2008, pp. 4853-4861.

Michael S. Lyons, et al., "Isolation of the Zebrafish Homologues for the *tie*-1 and *tie*-2 Endothelium-Specific Receptor Tyrosine Kinases", Developmental Dynamics, vol. 212, 1998, pp. 133-140.

KG Peters et al., "Expression of Tie2/Tek in breast tumor vasculature provides a new marker for evaluation of tumor angiogenesis", British Journal of Cancer, vol. 77, No. 1, 1998, pp. 51-56.

Nina Jones et al., "Identification of Tek/Tie2 Binding Partners", The Journal of Biological Chemistry, vol. 274, No. 43, Oct. 1999, pp. 30896-30905.

\* cited by examiner

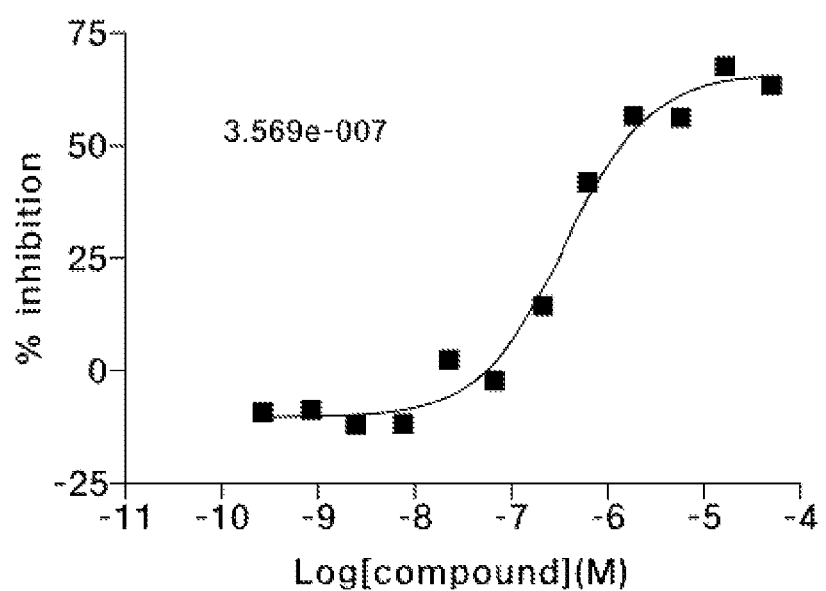

1,6-DISUBSTITUTED INDOLE COMPOUNDS AS PROTEIN KINASE INHIBITORS

CROSS-REFERENCE TO RELATED APPLICATION

This application claims the benefit under 35 U.S.C. Section 371, of PCT International Application No. PCT/KR2010/007205, filed Oct. 20, 2010, the disclosures of which are hereby incorporated by reference.

TECHNICAL FIELD

The present invention relates to a 1,6-substituted indole compound having a protein kinase inhibition activity, a pharmaceutically acceptable salt, and a pharmaceutical composition for prevention and treatment of cancers caused by abnormal cell growth including the compound as an effective ingredient.

BACKGROUND ART

A protein kinase is an enzyme which catalyzes phosphorylation of hydroxyl groups on tyrosine, serine and threonine residues of proteins. It plays an important role in signal transduction of growth factors involved in growth, differentiation and proliferation of cells.

To maintain homeostasis, it is necessary to keep good balance in turning on and off of the signal transduction system. However, mutation or overexpression of specific protein kinases disrupts the signal transduction system in normal cells and causes various diseases including cancers, inflammations, metabolic diseases, brain diseases, or the like. Typical protein kinases that lead to diseases caused by abnormal cell growth include Raf, KDR, Fms, Tie2, SAPK2a, Ret, Abl, Abl (T315I), ALK, Aurora A, Bmx, CDK/cyclinE, Kit, Src, EGFR, EphA1, FGFR3, Flt3, Fms, IGF-1R, IKKb, IR, Itk, JAK2, KDR, Met, mTOR, PDGFRa, Plk1, Ret, Syk, Tie2, TrtB, etc.

It is estimated that there are 518 different kinds of protein kinase genes in humans constituting about 1.7% of the entire human genes [Manning et al., *Science*, 2002, 298, 1912]. Human protein kinases are largely divided into tyrosine-specific protein kinases and serine/threonine-specific protein kinase. The tyrosine-specific protein kinases may be divided into 58 receptor tyrosine kinases, which are grouped into 20 subfamilies, and 32 cytoplasmic/non-receptor tyrosine kinases, which are grouped into 10 subfamilies. The receptor tyrosine kinase has an extracellular domain capable of binding to a growth factor and a cytoplasmic active site that can phosphorylate the tyrosine residue. When a growth factor binds to the extracellular growth factor receptor site of the receptor tyrosine kinase, the receptor tyrosine kinase forms a dimer and the tyrosine residues in the cytoplasm are autophosphorylated. Then, the downstream proteins are sequentially phosphorylated, and as the signal transduction proceeds in the nucleus, the transcription factors that induce cancer are overexpressed in the end.

Raf is a serine/threonine (Ser/Thr)-specific protein kinase and serves the role of transmitting biological signals from activated growth factor receptors at the cell membrane into the nucleus. The mitogen-activated protein kinase (MAPK) signal transduction system is essential in cellular proliferation, division, survival, apoptosis, and the like. The MAPK signal transduction system largely consists of three kinase phosphorylation processes—i.e., sequential phosphorylation of MAPK kinase kinase (MAPKKK), MAPK kinase (MAPKK) and MAPK. Raf is a MAPKKK, MEK is a MAPKK, and the extracellular signal-regulated kinase (ERIC) is a MAPK. When the receptor is activated, the small GTP-binding protein, Ras, is activated and the MAPK signal transduction into the nucleus is performed through sequential phosphorylation of Raf-MEK-ERK.

The Ras oncogene (especially k-Ras) in a permanently activated state is closely related to the onset of solid cancers such as pancreatic cancer (~90%), rectal cancer (~45%), liver cancer (about 30%), non-small cell lung cancer (35%), renal cancer (~10%), or the like.

If Raf-1 binds to activated Ras, serine 338 of Raf-1 is phosphorylated [Avruch, *J. Recent Progress in Hormone Research*, 2001, 56, 127] and the Raf-1 is activated. In contrast, if 14-3-3 protein binds to Raf-1 with phosphorylated serine 259, the Raf-1 is inactivated.

The Raf kinase is also involved in the nuclear factor-κB (NF-κB) signal transduction system, which plays a key role in immune responses and inflammations [Caraglia, M. et al, *Annals of Oncology*, 2006, 17, 124]. That is, Raf phosphorylates inactivated IkB protein and induces migration of NF-κB protein into the nucleus, thereby promoting the transcription factor that inhibits apoptosis.

Another apoptosis inhibition mechanism of Raf is as follows. Raf forms a dimer together with Bcl-2 and is translocated into the mitochondria. There, it phosphorylates Bad, thereby initiating apoptosis inhibition by Bcl-2. Accordingly, Raf is immunoprecipitated along with Bcl-2 [Yuryev, A. et al, *Mol. Cell. Biol.*, 2000, 20, 4870].

The three subtypes of Raf protein (A-Raf, B-Raf and C-Raf/Raf-1) have three conserved regions (CR1, CR2 and CR3) at the N-terminal regulatory domain and the C-terminal kinase domain. CR1 includes a Ras-binding domain (RBD) such as the cysteine-rich domain (CRD), CR2 includes a 14-3-3 protein-binding site (e.g., serine 259 of Raf-1), and CR3 includes a catalytic domain [Tran et al., *J. Biol. Chem.*, 2005, 280, 16244] and two activation segment phosphorylation sites (threonine 491 and serine 494 of Raf-1) [Wellbrock, C. *Nature Reviews Molecular Cell Biology*, 2004, 5, 875]. The three subtypes of Raf protein are expressed in different tissues. Whereas C-Raf is expressed in almost all tissues, A-Raf is mainly expressed in urogenital tissues (e.g., kidney, uterus and prostate gland) and B-Raf is mainly expressed in nervous, splenic and hematopoietic tissues [Jaiswal, R. K. et al, *J. Biol. Chem.*, 1966, 271, 23626].

Mutation of B-Raf is associated with about 7% of all human cancers. Especially, the mutation of B-Raf is observed with high frequency (~70%) in melanoma, which is a type of skin cancer. Among the mutations of B-Raf, the B-Raf-V600E mutation, i.e. a point mutation with valine 600 of exon 15 being replaced by glutamic acid, mainly (~90%) induce melanoma [Davies, H. et al, *Nature* 2002, 417, 949]. When compared with wild-type B-Raf, B-Raf-V600E has an in vitro kinase of about 500 times. Accordingly, B-Raf-V600E induces hyperactivation of the MAPK signal transduction and leads to cancer. The reason why B-Raf-V600E has such a high kinase activity is as follows. The glutamic acid 600 replaced by the point mutation mimics a phosphate group between the phosphorylation sites (threonine 598 and serine 601) located at the activation segment and, thereby, induces structural conformation of the permanently activated B-Raf kinase domain [Tuveson, D. A., *Cancer Cell*, 2003, 4, 95]. Up to the present, about 40 B-Raf mutations (mainly occur at the activation segment and the glycine-rich C-loop of the catalytic domain). However, occurrence of mutations other than V600E is fairly infrequent. In rectal cancer, about 10% of B-Raf mutations occur at the G-loop of the catalytic domain [Rajagopalan et al., *Nature* 2002 418, 934].

Although B-Raf has an auto-inhibition domain at the N-terminal, B-Raf becomes permanently activated when activated H-Ras binds thereto. This is caused by phosphorylation of serine 445. The phosphorylation of serine 338 of C-Raf corresponds to that of serine 445 of B-Raf. The B-Raf V600E mutation inhibits the auto-inhibition mechanism of B-Raf and turns it permanently activated.

The B-Raf-V600E mutation is also observed at high frequency (about 50%) in papillary thyroid cancer [Salvatore, G. *J. Clin. Endocrinol. Metab.* 2004, 89, 5175]. Also, the B-Raf-V600E is closely related with the onset of colon cancer (about 20%) and uterine cancer (about 30%).

Also, hyperactivation of C-Raf without oncogenic mutation is observed in renal carcinoma (about 50%) and hepatocellular carcinoma (about 100%).

Sorafenib (BAY 43-9006, marketed as Nexavar) developed by Bayer and Onyx strongly inhibit C-Raf and both wild-type and mutant B-Raf. Further, sorafenib inhibits activity of the receptor tyrosine kinases, such as platelet-derived growth factor receptor, vascular endothelial growth factor receptors 1/2/3, fibroblast growth factor receptor, Flt-3, c-Kit, RET, etc. It inhibits the kinase by stabilizing the DGF motif of the kinase domain to have an inactive conformation [Wan, P. T. et. al. *Cell,* 2004, 116, 855]. Sorafenib was approved as a treatment for advanced renal cell carcinoma in 2005. The therapeutic effect of sorafenib on renal cancer originates from to the inhibition of vascular endothelial growth factor receptors 1/2/3 and other kinases rather than the inhibition of Raf. In the clinical trial phase II, a maximum allowed administration dose of sorafenib was 400 mg (twice a day). Administration of 600 mg (twice a day) of sorafenib may lead to grade 3 skin toxicity. Frequent adverse effects of sorafenib include hand-foot syndromes such as peeling of skin, rash and edema. In 2008, sorafenib was approved as a treatment for hepatocellular carcinoma (HCC). In addition, sorafenib showed therapeutic effect for intractable thyroid cancer, hormone-refractory prostate cancer and breast cancer in clinical trial phase II. However, sorafenib shows no therapeutic effect on the skin cancer melanoma.

PLX4720, a 7-azaindole derivative developed by Plexxikon, induces apoptosis of melanoma cells such as 1205Lu (Raf-V660E overexpressed cells) [Tsai, J. et. al., *PNAS,* 2008, 105, 3041]. PLX4720 is a potent inhibitor of Raf-V660E kinase activity ($IC_{50}$=13 nM) and also inhibits the proliferation of A375 melanoma cells ($IC_{50}$=0.5 μM).

CHIR265 developed by Novartis and Chiron also strongly inhibits the kinase activity of B-Raf-V600E ($IC_{50}$=19 nM), KDR ($IC_{50}$=70 nM), PDGFR-b ($IC_{50}$=30 nM) and c-Kit ($IC_{50}$=20 nM). CHIR265 is currently in clinical trial phase I for melanoma patients.

Resistance to Raf inhibitors is an emerging issue. Montagut et al. explained the mechanism of resistance to the Raf inhibitor by culturing M14 cells (human melanoma cells) with B-Raf-V600E mutation in the presence of a Raf inhibitor (AZ628) and acquiring clones resistant to the Raf inhibitor. Inhibition of B-Raf results in increased expression of C-Raf protein and decreased inhibitory effect on B-Raf-V600E. Meanwhile, the melanoma cells resistant to the Raf inhibitor (AZ628) exhibit increased susceptibility to the HSP90 inhibitor geldanamycin. Thus, inhibition of HSP90 may be a way to overcome the resistance to the Raf inhibitor [Montagut, C. Cancer Research, 2008, 68, 4853].

Vascular endothelial growth factor receptors (VEGFRs) are receptor tyrosine kinases (RTKs) and important regulatory factors of angiogenesis. They are involved in the formation of blood vessels and lymphatic vessels and in homeostasis, and exert important effects on nerve cell. Vascular endothelial growth factor (VEGF) is produced mostly by vascular endothelial cells, hematopoietic cells and stromal cells under a hypoxic condition or by stimulations from growth factors such as TGF, interleukin and PDGF. VEGF binds to VEGFR-1, -2 and -3. Each VEGF isoform binds to a specific receptor, thereby inducing the formation of a receptor homozygote or heterozygote, and activates each signal transduction system. The signal specificity of VEGFR is further fine-tuned by co-receptors such as neuropilin, heparan sulfate, integrin, cadherin, or the like.

The biological function of VEGF is mediated by type III RTK, VEGFR-1 (Flt-1), VEGFR-2 (KDR/Flk-1) and VEGFR-3 (Flt-4). VEGFR is closely related to Fms, Kit and PDGFR. Each VEGF binds to specific receptors. VEGF-A binds to VEGFR-1, -2 and receptor zygote, whereas VEGF-C binds to VEGFR-2, -3. PIGF and VEGF-B interact exclusively with VEGFR-1, and VEGF-E interacts only with VEGFR-2. VEGF-F interacts with VEGFR-1 or -2. Whereas VEGF-A, -B and PIGF are preferentially required for the formation of blood vessels, VEGF-C and -D are essential in the formation of lymphatic vessels. Angiogenesis is essential in the proliferation and transition of tumors, since it supplies nutrients and oxygen to the tumors and provides channels for transition to cancer cells. Normally, angiogenesis is balanced by angiogenic stimulators and angiogenic inhibitors. If the balance is broken, as in cancer cells, the growth factor that affects the vascular endothelial cells most, i.e. VEGF, activates its receptor, VEGFR. At present, various researches are under way on the inhibitors that inhibit the receptor tyrosine kinase of VEGF using low molecular weight synthetic substances, which are advantageous in that they are applicable also to solid tumors and have fewer side effects because they inhibit angiogenesis in the cancer cells only.

Tie2 is a kind of receptor tyrosine kinase and is deeply involved with angiogenesis and vasculature. The domain structure of Tie2 is very highly conserved in all vertebrates [Lyons et al., 1998]. The ligand of Tie2 is angiopoietin (Ang). Ang2 does not induce autophosphorylation of Tie2, but interferes with the activation of Tie2 by Ang1. In endothelial cells, the activation of Tie2 by Ang2 induces activation of PI3K-Akt [Jones et al., 1999]. In the mitogen-activated protein kinase (MAPK) signal transduction pathway, which is the main signal transduction system of Tie2, the adaptor protein GRB2 and the protein tyrosine phosphatase SHP2 play a key role in dimerization of the Tie2 receptor tyrosine kinase through autophosphorylation. Ang/Tie2 and the VEGF signal transduction pathway are important in angiogenesis of cancer cells. Tie2 is expressed in vascular endothelial cells. Especially, the expression increases remarkably at the site invaded by cancer cell. Overexpression of Tie2 was observed in breast cancer [Peters et al., 1998] and also in uterine cancer, liver cancer and brain cancer.

Several compounds with an indole structure have been synthesized. However, the indole compound of the present invention with specific substituents at the 1- and 6-positions of indole, particularly the compound with a specific substituent at the phenyl group of the 6-position, is a novel compound. Thus, of course, the inhibition activity against various protein kinases or the possibility as an agent for treatment and prevention of cancers of the 1,6-substituted indole compound has never been predicted in any literature.

DISCLOSURE

Technical Problem

An object of the present invention is to provide a novel 1,6-substituted indole compound having specific substituents at the 1- and 6-positions of indole or a pharmaceutically acceptable salt thereof.

Another object of the present invention is to provide a pharmaceutical composition for prevention and treatment of cancers comprising the novel 1,6-substituted indole compound or a pharmaceutically acceptable salt thereof as an effective ingredient.

Still another object of the present invention is to provide a method for preparing the novel 1,6-substituted indole compound.

Technical Solution

The present invention provides a 1,6-substituted indole compound represented by Chemical Formula 1, a pharmaceutically acceptable salt thereof, a hydrate thereof or a solvate thereof.

[Chemical Formula 1]

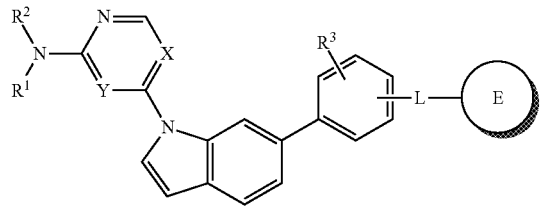

wherein

X is selected from the group consisting of N and CH;

Y is selected from the group consisting of N and $CR^a$;

L is selected from the group consisting of $—NR^4C(O)—$, $—C(O)NR^5—$, $—NR^4C(O)NR^5—$ and $—NR^4S(O)_2—$;

$R^a$ is hydrogen or linked with $R^1$ to form a 5- to 7-membered ring;

$R^1$ is selected from the group consisting of hydrogen, linear, branched or cyclic $C_1$-$C_6$ alkyl, $C_1$-$C_6$ alkyl substituted with a 5- to 7-membered substituted or unsubstituted heterocycle containing 1 to 3 heteroatom(s) selected from nitrogen, oxygen and sulfur atoms, and $—C(O)R^4$;

$R^2$, $R^3$, $R^4$ and $R^5$ are independently selected from the group consisting of hydrogen and linear, branched or cyclic $C_1$-$C_6$ alkyl;

E is selected from the group consisting of linear, branched or cyclic saturated or unsaturated $C_1$-$C_6$ alkyl, 5- to 7-membered substituted or unsubstituted aryl, biaryl formed from two 5- to 7-membered substituted or unsubstituted aryls, 5- to 7-membered substituted or unsubstituted heteroaryl containing 1 to 3 heteroatom(s) selected from nitrogen, oxygen and sulfur atoms, and 5- to 7-membered substituted or unsubstituted heterocycle containing 1 to 3 heteroatom(s) selected from nitrogen, oxygen and sulfur atoms;

the aryl, heteroaryl, biaryl and heterocycle are independently substituted or unsubstituted with 1 to 3 substituent(s) selected from the group consisting of hydrogen, halogen; $—CN$; $—NO_2$; linear, branched or cyclic $C_1$-$C_6$ alkyl, $C_1$-$C_6$ haloalkyl containing 1 to 10 halogen atom(s), cyano $C_1$-$C_6$ alkyl, $—OR^6$, $—O(CH_2)_nNR^7R^8$ (wherein n is an integer from 1 to 6), $—NR^7R^8$, $—NR^6COR^7$, $—NR^5C(O)NR^7R^8$, $—C(O)R^7$, $—C(O)OR^7$, $—C(O)NR^7R^8$, $—C(O)NH(CH_2)_nNR^7R^8$, $—S(O)R^7$, $—S(O)_2R^7$, $—S(O)_2NR^7R^8$, 5- to 7-membered aryl, biaryl formed from two 5- to 7-membered aryls, 5- to 7-membered heteroaryl containing 1 to 3 heteroatom(s) selected from nitrogen, oxygen and sulfur atoms, and 5- to 7-membered heterocycle containing 1 to 3 heteroatom(s) selected from nitrogen, oxygen and sulfur atoms, wherein the aryl, biaryl, heteroaryl and heterocycle may be independently substituted with 1 to 3 substituent(s) selected from the group consisting of halogen, $C_1$-$C_6$ alkyl, and $C_1$-$C_6$ haloalkyl containing 1 to 10 halogen atom(s); and $R^6$, $R^7$ and $R^8$ are independently selected from the group consisting of hydrogen, halogen, linear, branched or cyclic saturated or unsaturated $C_1$-$C_6$ alkyl, 5- to 7-membered aryl, biaryl formed from two 5- to 7-membered aryls, 5- to 7-membered heteroaryl containing 1 to 3 heteroatom(s) selected from nitrogen, oxygen and sulfur atoms, and 5- to 7-membered heterocycle containing 1 to 3 heteroatom(s) selected from nitrogen, oxygen and sulfur atoms, or $R^7$ and $R^8$ of $NR^7R^8$ may form 5- to 7-membered heteroaryl or heterocycles containing a nitrogen atom or optionally, 1 to 3 other heteroatom(s), wherein the aryl, biaryl, heteroaryl and heterocycle may be independently substituted with 1 to 3 substituent(s) selected from the group consisting of halogen, $C_1$-$C_6$ alkyl, $C_1$-$C_6$ alkoxy, and $C_1$-$C_6$ haloalkyl containing 1 to 10 halogen atom(s).

Advantageous Effects

The 1,6-substituted indole compound represented by Chemical Formula 1, a pharmaceutically acceptable salt thereof, a hydrate thereof or a solvate thereof has superior capability of inhibiting the activity of protein kinases selected from Raf, KDR, Fms, Tie2, SAPK2a, Ret, Abl, Abl(T315I), ALK, Aurora A, Bmx, Src, EphA1, FGFR, Flt3, Itk, JAK2, Met, PDGFR, Plk, Ret, Syk and Trk, and is effective for preventing and treating cancers caused by abnormal cell growth.

Specifically, the diseases caused by abnormal cell growth that may be prevented or treated by the compound according to the present invention may include various cancers selected from stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma, fibroadenoma, etc.

DESCRIPTION OF DRAWING

The above and other objects, features and advantages of the present invention will become apparent from the following description of preferred embodiments given in conjunction with the accompanying drawing, in which:

FIG. 1 shows an inhibition activity of 1-(2-methoxyphenyl)-3-(3-(1-(6-(methylamino)pyrimidin-4-yl)-1H-indol-6-yl)phenyl)ure a (compound of Example 22) against A375P cells.

BEST MODE

Hereinafter, the embodiments of the present invention will be described in detail.

A pharmaceutically acceptable salt of the 1,6-substituted indole compound represented by Chemical Formula 1 may be prepared by a method commonly employed in the art. The pharmaceutically acceptable salt should be less toxic to the human body and should not have negative effects on the biological activity and physical and chemical properties of the mother compound. The pharmaceutically acceptable salt includes a free acid, an acid addition salt of a base compound represented by Chemical Formula 1, an alkali metal salt (e.g., a sodium salt), an alkaline earth metal salt (e.g., a calcium salt), an organic salt, an organic base addition salt of a carboxylic acid represented by Chemical Formula 1, and an amino acid addition salt. The free acid that may be used to prepare the pharmaceutically acceptable salt includes an inorganic acid or an organic acid. The inorganic acid may be hydrochloric acid, sulfuric acid, nitric acid, phosphoric acid, perchloric acid, bromic acid, or the like. The organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, or the like. The organic base that may be used to prepare the organic base addition salt includes tris(hydroxymethyl)methylamine, dicyclohexylamine, or the like. The amino acid that may be used to prepare the amino acid addition salt includes a naturally occurring amino acid such as alanine, glycine, etc.

The 1,6-substituted indole compound represented by Chemical Formula 1 includes, in addition to the pharmaceutically acceptable salts, all hydrates and solvates. The hydrate or the solvate may be prepared by dissolving the 1,6-substituted indole compound represented by Chemical Formula 1 in a water-miscible solvent such as methanol, ethanol, acetone and 1,4-dioxane, adding a free acid or a free base thereto, and then performing crystallization or recrystallization. Accordingly, the compound of the present invention includes, in addition to the compounds containing various amounts of water that can be prepared through, for example, lyophilization, stoichiometric solvates including hydrates.

Hereunder is given a detailed description about the substituents used to define the compound according to the present invention.

In the present invention, 'halogen atom' means a fluorine, chlorine, bromine or iodine atom.

In the present invention, 'alkyl' means a $C_1$-$C_6$ aliphatic saturated hydrocarbon group, including methyl, ethyl, n-propyl, i-propyl, cyclopropyl, n-butyl, i-butyl, t-butyl, cyclobutyl, cyclopropylmethyl, n-pentyl, i-pentyl, neopentyl, t-pentyl, cyclopentyl, cyclobutylmethyl, n-hexyl, i-hexyl, cyclohexyl, cyclopentylmethyl, or the like.

In the present invention, 'haloalkyl' means an alkyl group with one or more hydrogen(s) substituted by halogen atom(s), such as trifluoromethyl.

In the present invention, 'alkoxy' means a hydroxyl group with the hydrogen substituted by a $C_1$-$C_6$ alkyl group substituent, such as methoxy, ethoxy, n-propoxy, i-propoxy, n-butoxy, i-butoxy and t-butoxy.

In the present invention, 'aryl' means a mono-, bi- or tricyclic aromatic hydrocarbon group, such as phenyl, naphthyl, anthracenyl, phenanthrenyl, or the like.

In the present invention, 'biaryl' means an aromatic hydrocarbon group formed from two aryl groups, such as biphenyl, phenoxyphenyl, benzoylphenyl, phenyldiazenylphenyl, or the like.

In the present invention, 'heteroaryl' means a mono-, bi- or tricyclic aromatic heterohydrocarbon group containing one or more heteroatom(s) selected from oxygen, nitrogen and sulfur atoms, such as pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, pyridinyl, pyrazinyl, pyridazinyl, pyrimidinyl, triazolyl, indolyl, isoindolyl, benzofuranyl, benzofurazanyl, dibenzofuranyl, isobenzofuranyl, indazolyl, benzimidazolyl, benzoxazolyl, benzisoxazolyl, benzothiazolyl, dibenzothiophenyl, naphthyridyl, benzisothiazolyl, quinolinyl, isoquinolinyl, quinoxalinyl, phthalazinyl, phthalazinyl, quinazolinyl, etc.

In the present invention, 'heterocycle' means a heterohydrocarbon ring containing one or more heteroatom(s), such as morpholinyl, piperidinyl, piperazinyl, N-protected piperazinyl, etc.

Preferably, in the 1,6-substituted indole compound represented by Chemical Formula 1, X is selected from the group consisting of N and CH; Y is selected from the group consisting of N and $CR^a$; L is selected from the group consisting of —$NR^4C(O)$—, —$C(O)NR^5$—, —$NR^4C(O)NR^5$— and —$NR^4S(O)_2$—; $R^a$ is hydrogen or is linked with $R^1$ to form a 5- to 7-membered ring; $R^1$ is selected from the group consisting of hydrogen, linear, branched or cyclic $C_1$-$C_6$ alkyl, $C_1$-$C_6$ alkylmorpholino and —$C(O)R^4$; $R^2$, $R^3$, $R^4$ and $R^5$ are independently selected from the group consisting of hydrogen and linear, branched or cyclic $C_1$-$C_6$ alkyl; E is selected from the group consisting of linear, branched or cyclic saturated or unsaturated $C_1$-$C_6$ alkyl, substituted or unsubstituted phenyl, substituted or unsubstituted furanyl, substituted or unsubstituted oxazolyl, substituted or unsubstituted isoxazolyl, substituted or unsubstituted pyrazolyl, substituted or unsubstituted thiazolyl, and substituted or unsubstituted thiophenyl; and the substituted phenyl, furanyl, oxazolyl, isoxazolyl, pyrazolyl, thiazolyl are thiophenyl are independently substituted or unsubstituted with 1 to 3 substituent(s) selected from the group consisting of hydrogen, halogen, linear, branched or cyclic $C_1$-$C_6$ alkyl, $C_1$-$C_6$ haloalkyl containing 1 to 10 halogen atom(s), cyano $C_1$-$C_6$ alkyl, $C_1$-$C_6$ alkoxy, N—($C_1$-$C_6$ alkyl)piperidinyloxy, morpholino, substituted or unsubstituted phenyl, substituted or unsubstituted pyridinyl, and substituted or unsubstituted imidazolyl, wherein the substituted phenyl, pyridinyl or imidazolyl are independently substituted with 1 to 3 substituent(s) selected from the group consisting of halogen, $C_1$-$C_6$ alkyl, $C_1$-$C_6$ alkoxy, and $C_1$-$C_6$ haloalkyl containing 1 to 10 halogen atom(s).

More preferably, in the 1,6-substituted indole compound represented by Chemical Formula 1, X is N; Y is selected from the group consisting of N and $CR^a$; L is selected from the group consisting of —NHC(O)—, —NHC(O)NH— and —$NHS(O)_2$—; $R^a$ is hydrogen or linked with $R^1$ to form a pyrrolo[2,3-d]pyrimidine ring; $R^1$ is selected from the group consisting of hydrogen, methyl, ethyl, cyclopropyl, morpholinoethyl and —C(O)-cyclopropyl; $R^2$ and $R^3$ are independently selected from the group consisting of hydrogen and methyl; E is selected from the group consisting of methyl, ethyl, cyclopropyl, cyclohexyl, substituted or unsubstituted phenyl, substituted or unsubstituted furanyl, substituted or unsubstituted oxazolyl, substituted or unsubstituted isoxazolyl, substituted or unsubstituted pyrazolyl, substituted or unsubstituted thiazolyl, and substituted or unsubstituted thiophenyl; and the substituted phenyl, furanyl, oxazolyl, isoxazolyl, pyrazolyl, thiazolyl and thiophenyl are independently substituted or unsubstituted with 1 to 3 substituent(s) selected from the group consisting of hydrogen, chloro, fluoro, bromo, methyl, trifluoromethyl, cyanopropan-2-yl, methoxy, methylpiperidinyloxy, morpholino, substituted or unsubstituted phenyl, substituted or unsubstituted pyridinyl, and substituted or unsubstituted imidazolyl, wherein the substituted phenyl, pyridinyl or imidazolyl are independently substituted with 1 to 3 substituent(s) selected from the group consisting of chloro, methyl, methoxy and trifluoromethyl.

Particularly preferably, in the 1,6-substituted indole compound represented by Chemical Formula 1, X is N; Y is CR$^a$; L is —NHC(O)— or —NHC(O)NH—; R$^a$ is hydrogen or linked with R$^1$ to form a pyrrolo[2,3-d]pyrimidine ring; R$^1$ is hydrogen, methyl, cyclopropyl, morpholinoethyl or —C(O)-cyclopropyl; R$^2$ and R$^3$ are independently hydrogen or methyl; and E is cyclohexyl, phenyl, 2-methoxyphenyl, 3-chloro-4-trifluorophenyl, 3-trifluoro-4-chlorophenyl, 3-morpholino-5-trifluorophenyl, 3-(4-methyl-1H-imidazol-1-yl)-5-trifluorophenyl, 3-(2-cyanopropan-2-yl)phenyl or 5-methylisoxazol-3-yl.

Specific examples of the 1,6-substituted indole compound represented by
Chemical Formula 1 include:

1-(3-(1-(6-aminopyrimidin-4-)-1H-indol-6-yl)phenyl)-3-(2-methoxyphenyl)urea;
1-(3-(1-(6-aminopyrimidin-4-yl)-1H-indol-6-yl)phenyl)-3-(3-chloro-4-(trifluoromethyl)phenyl)urea;
1-(3-(1-(6-aminopyrimidin-4-yl)-1H-indol-6-yl)phenyl)-3-(2-fluorophenyl)urea;
1-(3-(1-(6-aminopyrimidin-4-yl)-1H-indol-6-yl)phenyl)-3-(3,4-dichlorophenyl)urea;
1-(3-(1-(6-aminopyrimidin-4-yl)-1H-indol-6-yl)phenyl)-3-cyclohexylurea;
N-(3-(1-(6-aminopyrimidin-4-yl)-1H-indol-6-yl)phenyl)-4-chloro-3-(trifluoromethyl)benzamide;
N-(3-(1-(6-aminopyrimidin-4-yl)-1H-indol-6-yl)phenyl)-3-morpholino-5-(trifluoro methyl)benzamide;
N-(3-(1-(6-aminopyrimidin-4-yl)-1H-indol-6-yl)phenyl)-3-(4-methyl-1H-imidazol-1-yl)-5-(trifluoromethyl)benzamide;
N-(3-(1-(6-aminopyrimidin-4-yl)-1H-indol-6-yl)phenyl)-3-(2-cyanopropan-2-yl)benzamide;
N-(3-(1-(6-aminopyrimidin-4-yl)-1H-indol-6-yl)phenyl)-5-(4-methoxyphenyl)furan-2-carboxamide;
N-(3-(1-(6-aminopyrimidin-4-yl-1H-indol-6-yl)phenyl)-5-(2-chloro-5-(trifluoromethyl)phenyl)furan-2-carboxamide;
N-(3-(1-(6-aminopyrimidin-4-yl)-1H-indol-6-yl)phenyl)-2,5-dimethylfuran-3-carboxamide;
N-(3-(1-(6-aminopyrimidin-4-yl)-1H-indol-6-yl)phenyl)-5-methylisoxazol-3-carboxamide;
N-(3-(1-(6-aminopyrimidin-4-yl)-1H-indol-6-yl)phenyl)-5-(4-chlorophenyl)isoxazol-3-carboxamide;
N-(3-(1-(6-aminopyrimidin-4-yl)-1H-indol-6-yl)phenyl)thiazol-4-carboxamide;
N-(3-(1-(6-aminopyrimidin-4-yl)-1H-indol-6-yl)phenyl)-2-(pyridin-4-yl)thiazol-4-carboxamide;
N-(3-(1-(6-aminopyrimidin-4-yl)-1H-indol-6-yl)phenyl)-1-phenyl-5-(trifluoromethyl)-1H-pyrazol-4-carboxamide;
N-(3-(1-(6-aminopyrimidin-4-yl)-1H-indol-6-yl)phenyl)-5-bromothiophen-2-carboxamide;
N-(3-(1-(6-aminopyrimidin-4-yl)-1H-indol-6-yl)phenyl)-4-(1-methylpiperidin-4-yloxy)-3-(trifluoromethyl)benzamide;
N-(3-(1-(6-aminopyrimidin-4-yl)-1H-indol-6-yl)phenyl)-4-methylbenzenesulfonamide;
1-(3-(1-(6-aminopyrimidin-4-yl)-1H-indol-6-yl)-4-methylphenyl)-3-(2-methoxyphenyl)urea;
1-(2-methoxyphenyl)-3-(3-(1-(6-(methylamino)pyrimidin-4-yl)-1H-indol-6-yl)phenyl)urea;
1-(3-(1-(6-(cyclopropylamino)pyrimidin-4-yl)-1H-indol-6-yl)phenyl)-3-(2-methoxyphenyl)urea;
1-(2-methoxyphenyl)-3-(3-(1-(6-(2-morpholinoethylamino)pyrimidin-4-yl)-1H-indol-6-yl)phenyl)urea;
1-(3-(1-(2-aminopyrimidin-4-yl)-1H-indol-6-yl)phenyl)-3-(2-methoxyphenyl)urea;
N-(6-(6-(3-(3-(2-methoxyphenyl)ureido)phenyl)-1H-indol-1-yl)pyrimidin-4-yl)cyclopropanecarboxamide;
N-(6-(6-(3-(3-(2-fluorophenyl)ureido)phenyl)-1H-indol-1-yl)pyrimidin-4-yl)cyclopropanecarboxamide;
N-(6-(6-(3-(3-(3,4-dichlorophenyl)ureido)phenyl)-1H-indol-1-yl)pyrimidin-4-yl)cyclopropanecarboxamide;
N-(6-(6-(3-(3-cyclohexylureido)phenyl)-1H-indol-1-yl)pyrimidin-4-yl)cyclopropanecarboxamide;
4-chloro-N-(3-(1-(6-(cyclopropanecarboxamido)pyrimidin-4-yl)-1H-indol-6-yl)phenyl)-3-(trifluoromethyl)benzamide;
N-(3-(1-(6-(cyclopropanecarboxamido)pyrimidin-4-yl)-1H-indol-6-yl)phenyl)-3-morpholino-5-(trifluoromethyl)benzamide;
N-(3-(1-(6-(cyclopropanecarboxamido)pyrimidin-4-yl)-1H-indol-6-yl)phenyl)-3-(4-methyl-1H-imidazol-1-yl)-5-(trifluoromethyl)benzamide;
3-(2-cyanopropan-2-yl)-N-(3-(1-(6-(cyclopropanecarboxamido)pyrimidin-4-yl)-1H-indol-6-yl)phenyl)benzamide;
N-(4-(6-(3-(3-(2-methoxyphenyl)ureido)phenyl)-1H-indol-1-yl)pyrimidin-2-yl)cyclopropanecarboxamide;
N-(6-(6-(5-(3-(2-methoxyphenyl)ureido)-2-methylphenyl)-1H-indol-1-yl)pyrimidin-4-yl)cyclopropanecarboxamide;
1-(3-(1-(7H-pyrrolo[2,3-d]pyrimidin-4-yl)-1H-indol-6-yl)phenyl)-3-(2-methoxyphenyl)urea; and
N-(3-(1-(7H-pyrrolo[2,3-d]pyrimidin-4-yl)-1H-indol-6-yl)phenyl)-4-chloro-3-(trifluoromethyl)benzamide.

The present invention also provides a method for preparing the 2 indole compound represented by Chemical Formula 1. A typical example is Scheme 1.

According to Scheme 1, the indole compound represented by Chemical Formula 1 is prepared by a 2-step process of introducing various -L-E substituents at the substituted phenyl group of the C-6 position of indole.

That is to say, it may be prepared by: reducing a nitro compound represented by Chemical Formula 2 to prepared an amine compound represented by Chemical Formula 3 (Step 1-1); and subjecting the amine compound represented by Chemical Formula 3 to a coupling reaction with an isocyanate compound, a carboxylic acid compound, or a sulfonyl chloride compound represented by Chemical Formula 4 to prepare the 2,6-substituted indole compound represented by Chemical Formula 1 (Step 1-2):

[Scheme 1]

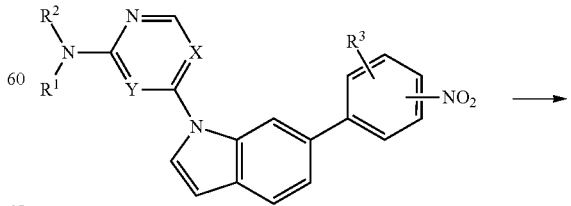

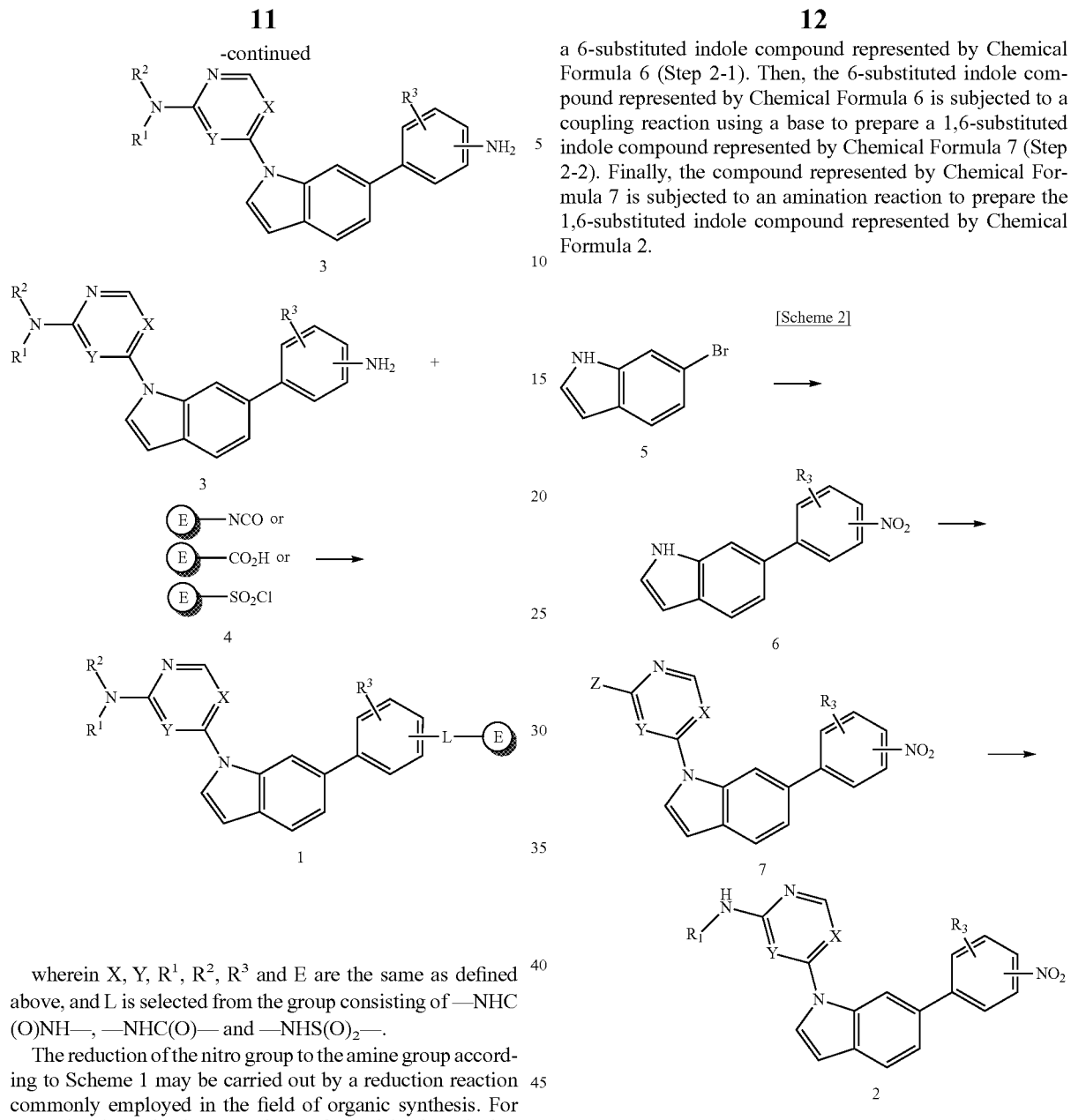

wherein X, Y, R¹, R², R³ and E are the same as defined above, and L is selected from the group consisting of —NHC(O)NH—, —NHC(O)— and —NHS(O)₂—.

The reduction of the nitro group to the amine group according to Scheme 1 may be carried out by a reduction reaction commonly employed in the field of organic synthesis. For example, the reduction may be performed by introducing hydrogen gas (H₂) in the presence of Raney nickel (Ni) or using stannous chloride (SnCl₂).

And, the coupling reaction according to Scheme 1 may be performed in a reaction solvent such as tetrahydrofuran or N,N-dimethylformamide in the presence or absence of an additive. The additive may be an organic base such as triethylamine, N,N-diisopropylethylamine, etc., an inorganic base such as K₂CO₃, NaHCO₃, etc., a peptide coupling reagent such as 1,3-dicyclohexylcarbodiimide (DCC), 1-ethyl-3-(3-dimethylaminopropyl)carbodiimide (EDC), 2-(1H-7-azabenzotriazol-1-yl)-1,1,3,3-tetramethyluronium hexafluorophosphate (HATU), etc., or a catalyst such as N-hydroxybenzotriazole (HOBt), N,N-dimethylaminopyridine (DMAP), etc.

The nitro compound represented by Chemical Formula 2, which is used as a starting material in Scheme 1, may be prepared according to Scheme 2.

According to Scheme 2, a 6-bromoindole compound represented by Chemical Formula 5 is subjected to a Suzuki coupling reaction using an organometal compound to prepare a 6-substituted indole compound represented by Chemical Formula 6 (Step 2-1). Then, the 6-substituted indole compound represented by Chemical Formula 6 is subjected to a coupling reaction using a base to prepare a 1,6-substituted indole compound represented by Chemical Formula 7 (Step 2-2). Finally, the compound represented by Chemical Formula 7 is subjected to an amination reaction to prepare the 1,6-substituted indole compound represented by Chemical Formula 2.

In Scheme 2, X, Y, R¹ and R³ are the same as defined above, and Z represents halogen or a leaving group.

In the Suzuki coupling reaction, Pd₂(dba)₃, Pd(OAc)₂, PdCl₂(PPh₃)₂, Pd(PPh₃)₄, etc. may be used as a metal catalyst. And, Xantphos (CAS number: 161265-03-8), Davephos (CAS number: 213697-53-1), Johnphos (CAS number: 224311-51-7), X-phos (CAS number: 564483-18-7), tert-butyl Xphos (CAS number: 564483-19-8), etc. may be used as a ligand. And, carbonate, sulfate, phosphate, alkoxide, etc. of an alkali metal or alkaline earth metal may be used as a base. Specific examples include K₂CO₃, CsCO₃, Na₂CO₃, K₃PO₄, NaOt-Bu, KOt-Bu, or the like. A commonly used organic solvent including tetrahydrofuran, dioxane, N,N-dimethylformamide, N,N-dimethylsulfoxide, 2-butanol, 2-pentanol, or the like may be used as a reaction solvent. The reaction temperature is maintained at 50 to 200° C., preferably at 80 to 150° C.

The 1,6-substituted indole compound represented by Chemical Formula 1, an isomer thereof, a pharmaceutically acceptable salt thereof, a solvate thereof and a hydrate thereof may be used as an agent for preventing or treating cancers caused by abnormal cell growth because they exhibit superior inhibition activity against various protein kinases, e.g., Raf, KDR, Fms, Tie2, SAPK2a, Ret, Abl, Abl(T315I), ALK, Aurora A, Bmx, Src, EphA1, FGFR, Flt3, Itk, JAK2, Met, PDGFR, Plk, Ret, Syk and Trk. Examples of the cancers caused by abnormal cell growth include various cancers such as stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma, fibroadenoma, or the like.

Accordingly, the present invention provides a pharmaceutical composition comprising the indole compound represented by Chemical Formula 1, a pharmaceutically acceptable salt thereof, a solvate thereof or a hydrate thereof as an effective ingredient, and an agent for preventing and treating various cancers caused by abnormal cell growth.

The pharmaceutical composition of the present invention comprises the indole compound represented by Chemical Formula 1, a pharmaceutically acceptable salt thereof, a solvate thereof or a hydrate thereof as an effective ingredient and may further include a commonly used, nontoxic, pharmaceutically acceptable carrier, adjuvant, excipient, or the like to prepare formulations commonly used in the pharmaceutical field, for example, formulations for oral administration such as tablet, capsule, troche, liquid, suspension, etc. and formulations for parenteral administration.

The excipient that may be used in the pharmaceutical composition of the present invention includes sweetener, binder, solubilizer, wetting agent, emulsifier, isotonic agent, adsorbent, disintegrant, antioxidant, preservative, lubricant, filler, aromatic, etc. For example, lactose, dextrose, sucrose, mannitol, sorbitol, cellulose, glycine, silica, talc, stearic acid, stearin, magnesium stearate, magnesium aluminum silicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, or the like may be used.

The administration dose of the compound according to the present invention may vary depending on the patient's age, body weight, sex and physical conditions, administration type, severity of disease, or the like. Based on an adult patient weighing 70 kg, the administration dose may be in general 0.01 to 1,000 mg/day. As per the decision by a physician or a pharmacist, the administration may be once to several times a day with predetermined time intervals.

MODE FOR INVENTION

The examples and experiments will now be described. The following examples and experiments are for illustrative purposes only and not intended to limit the scope of this disclosure.

The examples, formulation examples and test examples will now be described. However, the following examples, formulation examples and test examples are for illustrative purposes only and not intended to limit the scope of the present invention.

EXAMPLES

Example 1

1-(3-(1-(6-aminopyrimidin-4-)-1H-indol-6-yl)phenyl)-3-(2-methoxyphenyl)urea

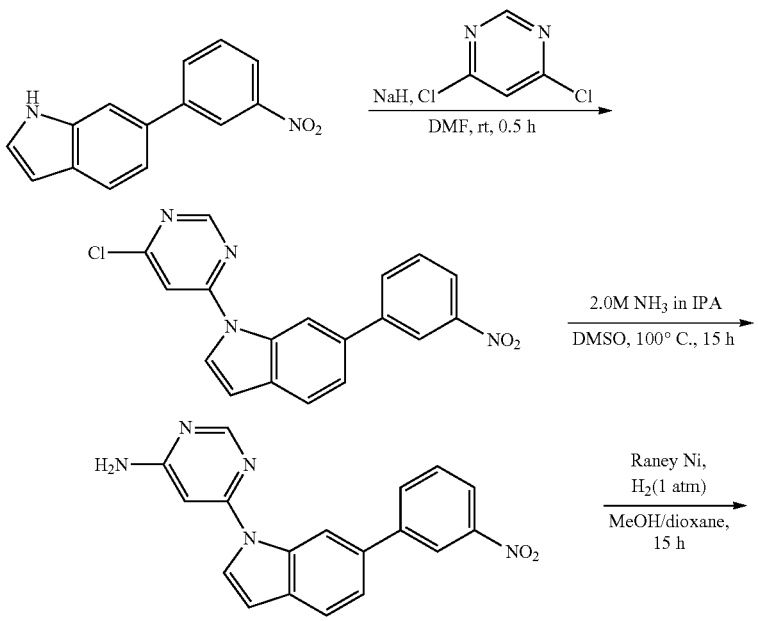

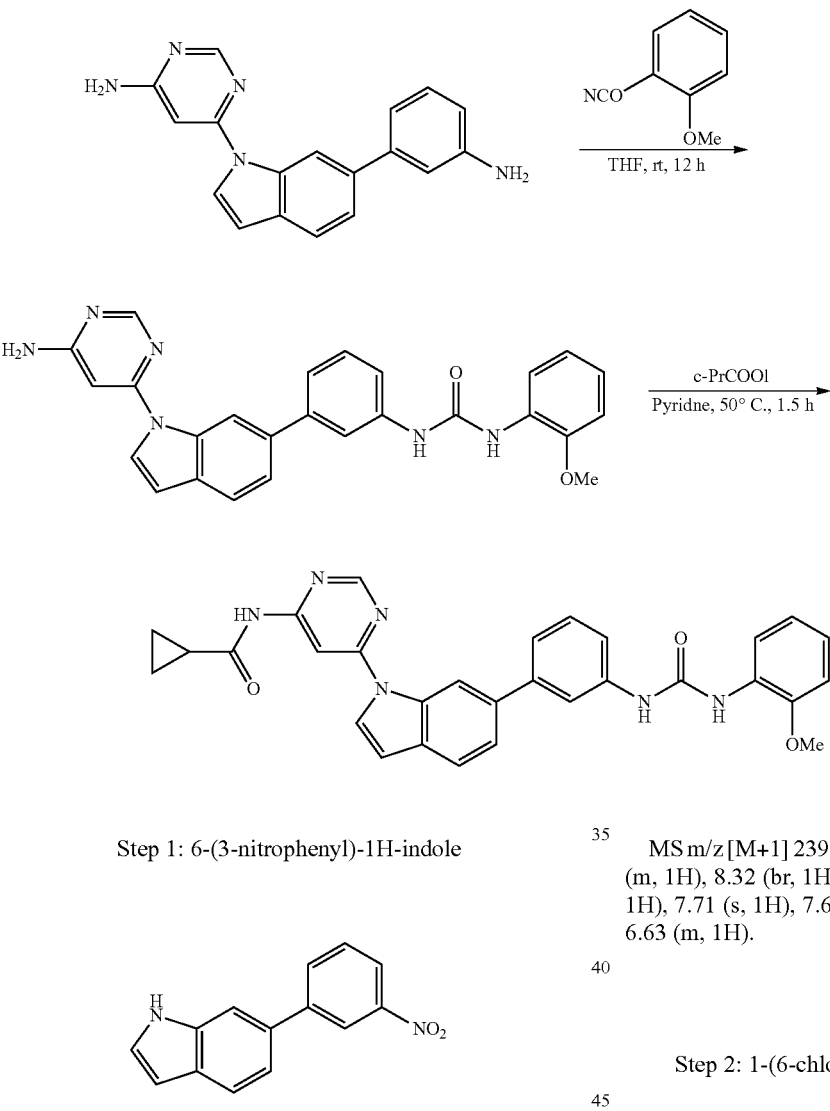

Step 1: 6-(3-nitrophenyl)-1H-indole

6-Bromo-1H-indole (1.00 g, 5.10 mmol) and potassium carbonate (1.41 g, 10.2 mmol) were dissolved in a DMF/water (4:1, 10 mL) mixture solution, and then the gas included in the mixture solution was removed using ultrasonic wave and nitrogen gas. After sequentially adding 3-nitrophenylboronic acid (853 mg, 5.61 mmol) and Pd(dppf)Cl$_2$ (416 mg, 0.51 mmol), the mixture was stirred at room temperature in a sealed reactor. 2 hours later, after adding ethyl acetate and water, the reaction solution was filtered through a diatomite pad. The organic layer was separated from the filtrate and the aqueous layer was extracted with ethyl acetate. The combined organic layer was dried with anhydrous magnesium sulfate and then concentrated. Purification of the residue by chromatography (silica gel, EA:Hx=1:4) yielded the target compound as white solid.

MS m/z [M+1] 239.18; $^1$H NMR (400 MHz, CDCl$_3$) d 8.52 (m, 1H), 8.32 (br, 1H), 8.17 (dd, 1H), 7.98 (d, 1H), 7.76 (d, 1H), 7.71 (s, 1H), 7.60 (t, 1H), 7.41 (dd, 1H), 7.31 (m, 1H), 6.63 (m, 1H).

Step 2: 1-(6-chloropyrimidin-4-yl)-6-(3-nitrophenyl)-1H-indole 6-(3-Nitrophenyl)-1H-indole (2 g, 8.39 mmol) and 4,6-dichloropyrimidine (1.25 g, 8.39 mmol) were dissolved in DMF (20 mL) and sodium hydride (60% in mineral oil, 671 mg, 16.78 mmol) was added at 0° C. 1 hour later, ice was added to the reaction solution and the mixture solution was added to ice water. The mixture solution was stirred at room temperature for 12 hours. Thus prepared solid was filtered, washed with water, and dried in the air. 1-(6-Chloropyrimidin-4-yl)-6-(3-nitrophenyl)-1H-indole (2.61 g) was yielded as yellow solid.

MS m/z [M+1] 350.91; $^1$H NMR (400 MHz, DMSO-$d_6$) d 9.01 (s, 1H), 8.96 (s, 1H), 8.45 (s, 1H), 8.32 (d, 1H), 8.26 (d, 1H), 8.21 (d, 1H), 8.19 (s, 1H), 7.81 (t, 1H), 7.75 (d, 1H), 7.65 (d, 1H), 6.96 (d, 1H).

Step 3: 6-(6-(3-nitrophenyl)-1H-indol-1-yl)pyrimidin-4-amine

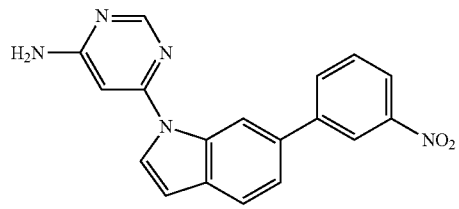 [SMILES: Nc1cc(-n2ccc3ccc(-c4cccc([N+](=O)[O-])c4)cc32)ncn1]

1-(6-Chloropyrimidin-4-yl)-6-(3-nitrophenyl)-1H-indole (1 g, 2.86 mmol) was dissolved in DMSO (15 mL) in a sealed reactor. After adding 2.0 M ammonia solution in isopropanol (15 mL, 30 mmol), the reaction mixture was stirred at 100° C. for 15 hours. After cooling to room temperature and adding water (70 mL), the reaction mixture was stirred at room temperature for 1 hour. Thus prepared solid was filtered, washed with water, and dried in the air. 6-(6-(3-Nitrophenyl)-1H-indol-1-yl)pyrimidin-4-amine (850 mg) was yielded as white solid.

MS m/z [M+1] 332.98; $^1$H NMR (400 MHz, DMSO-$d_6$) d 8.64 (s, 1H), 8.40 (d, 1H), 8.38 (s, 1H), 8.18 (d, 1H), 8.15 (d, 1H), 7.96 (s, 1H), 7.75 (t, 1H), 7.73 (d, 1H), 7.55 (d, 1H), 7.02 (s, 2H), 6.78 (d, 1H), 6.66 (s, 1H).

Step 4: 6-(6-(3-aminophenyl)-1H-indol-1-yl)pyrimidin-4-amine

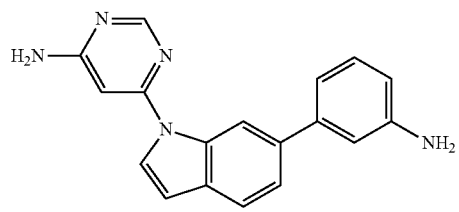

6-(6-(3-Nitrophenyl)-1H-indol-1-yl)pyrimidin-4-amine (400 mg, 1.21 mmol) was dissolved in methanol/dioxane (1:1, 6 mL) and Raney nickel was added. The mixture solution was stirred under hydrogen gas (1 atm) for 1.5 hours. The mixture solution was filtered through a diatomite pad, and the filtrate was concentrated under reduced pressure. After adding methylene chloride to the residue, thus prepared solid was filtered. 6-(6-(3-Aminophenyl)-1H-indol-1-yl)pyrimidin-4-amine (158 mg) was yielded as white solid. Concentration of the filtrate followed by column chromatography (silica gel, EA:Hx=1:1→MC:MeOH=20:1) further gave the target compound.

MS m/z [M+1] 302.09; $^1$H NMR (400 MHz, DMSO-$d_6$) d 8.48 (s, 1H), 8.41 (s, 1H), 7.92 (d, 1H), 7.66 (d, 1H), 7.36 (d, 1H), 7.11 (t, 1H), 7.06 (s, 2H), 6.87 (s, 1H), 6.80 (d, 1H), 6.76 (d, 1H), 6.67 (s, 1H), 6.54 (d, 1H), 5.16 (s, 2H).

Step 5: 1-(3-(1-(6-aminopyrimidin-4-)-1H-indol-6-yl)phenyl)-3-(2-methoxyphenyl)urea

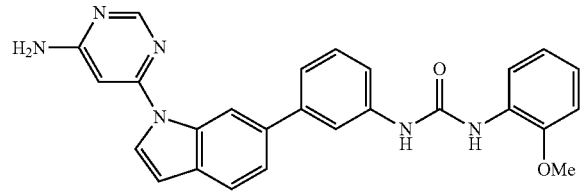

6-(6-(3-Aminophenyl)-1H-indol-1-yl)pyrimidin-4-amine (15 mg, 0.050 mmol) was dissolved in THF (1 mL). At room temperature, 2-methoxyphenyl isocyanate (7.8 μL, 0.075 mmol) was added. The reaction solution was stirred at room temperature. 15 hours later, the reaction mixture was concentrated under reduced pressure. Diethyl ether was added to solidify the residue. Thus prepared solid was filtered to obtain 1-(3-(1-(6-aminopyrimidin-4-)-1H-indol-6-yl)phenyl)-3-(2-methoxyphenyl)urea as white solid. Concentration of the filtrate followed by column chromatography (silica gel, EA:Hx=1:4→MC:MeOH=20:1) yielded the target compound.

MS m/z [M+1] 451.06; $^1$H NMR (400 MHz, DMSO-$d_6$) d 9.49 (s, 1H), 8.56 (s, 1H), 8.42 (s, 1H), 8.26 (s, 1H), 8.14 (d, 1H), 7.95 (d, 1H), 7.73 (d, 1H), 7.72 (s, 1H), 7.49 (d, 1H), 7.43 (d, 1H), 7.39 (t, 1H), 7.30 (d, 1H), 7.06 (s, 2H), 7.01 (d, 1H), 6.95 (d, 1H), 6.91 (t, 1H), 6.79 (t, 1H), 6.69 (s, 1H), 3.88 (s, 3H).

Example 2

1-(3-(1-(6-aminopyrimidin-4-yl)-1H-indol-6-yl)phenyl)-3-(3-chloro-4-(trifluoromethyl)phenyl)urea

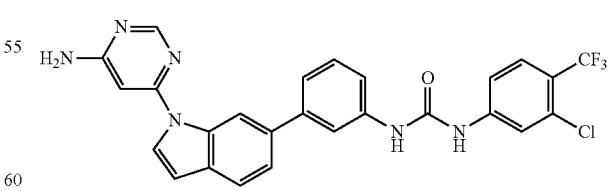

The target compound was prepared in the same manner as Example 1 using an appropriate starting material.

MS m/z [M+1] 522.98; $^1$H NMR (400 MHz, DMSO-$d_6$) d 9.24 (s, 1H), 9.01 (s, 1H), 8.58 (s, 1H), 8.43 (s, 1H), 8.12 (s, 1H), 7.95 (d, 1H), 7.77 (s, 1H), 7.72 (s, 1H), 7.65 (d, 1H), 7.60

(d, 1H), 7.47 (t, 1H), 7.44 (d, 1H), 7.41 (d, 1H), 7.34 (d, 1H), 7.15 (s, 2H), 6.80 (d, 1H), 6.70 (s, 1H).

Example 3

1-(3-(1-(6-aminopyrimidin-4-yl)-1H-indol-6-yl)phenyl)-3-(2-fluorophenyl)urea

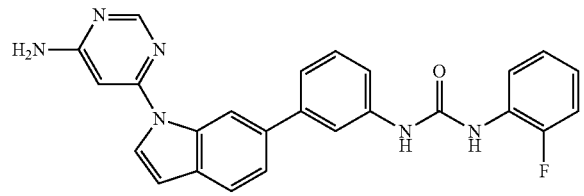 [SMILES: Nc1cc(-n2ccc3ccc(-c4cccc(NC(=O)Nc5ccccc5F)c4)cc32)ncn1]

The target compound was prepared in the same manner as Example 1 using an appropriate starting material.

MS m/z [M+1] 439.05; $^1$H NMR (400 MHz, DMSO-$d_6$) d 9.26 (s, 1H), 8.61 (s, 1H), 8.56 (s, 1H), 8.41 (s, 1H), 8.16 (t, 1H), 7.95 (d, 1H), 7.74 (s, 1H), 7.72 (d, 1H), 7.45 (d, 1H), 7.42 (d, 1H), 7.38 (d, 1H), 7.30 (d, 1H), 7.24 (t, 1H), 7.14 (t, 1H), 7.06 (s, 2H), 7.04 (d, 1H), 6.79 (d, 1H), 6.69 (s, 1H).

Example 4

1-(3-(1-(6-aminopyrimidin-4-yl)-1H-indol-6-yl)phenyl)-3-(3,4-dichlorophenyl)urea

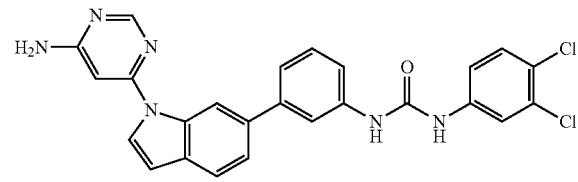 [SMILES: Nc1cc(-n2ccc3ccc(-c4cccc(NC(=O)Nc5ccc(Cl)c(Cl)c5)c4)cc32)ncn1]

The target compound was prepared in the same manner as Example 1 using an appropriate starting material.

MS m/z [M+1] 488.97; $^1$H NMR (400 MHz, DMSO-$d_6$) d 9.09 (s, 1H), 8.99 (s, 1H), 8.53 (s, 1H), 8.41 (s, 1H), 7.95 (d, 1H), 7.90 (s, 1H), 7.73 (d, 1H), 7.71 (s, 1H), 7.51 (d, 1H), 7.45 (t, 1H), 7.43 (d, 1H), 7.40 (d, 1H), 7.36 (d, 1H), 7.33 (d, 1H), 7.05 (s, 2H), 6.79 (d, 1H), 6.68 (s, 1H).

Example 5

1-(3-(1-(6-aminopyrimidin-4-yl)-1H-indol-6-yl)phenyl)-3-cyclohexylurea

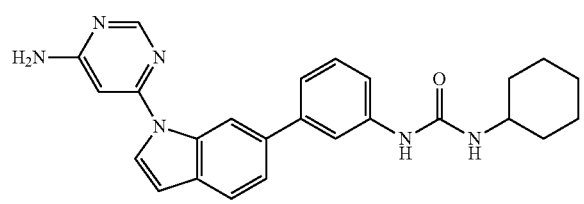 [SMILES: Nc1cc(-n2ccc3ccc(-c4cccc(NC(=O)NC5CCCCC5)c4)cc32)ncn1]

The target compound was prepared in the same manner as Example 1 using an appropriate starting material.

MS m/z [M+1] 427.12; $^1$H NMR (400 MHz, DMSO-$d_6$) d 8.52 (s, 1H), 8.45 (s, 1H), 8.41 (s, 1H), 7.94 (d, 1H), 7.69 (d, 1H), 7.65 (s, 1H), 7.41 (s, 1H), 7.38 (d, 1H), 7.31 (t, 1H), 7.19 (d, 1H), 7.06 (s, 2H), 6.78 (d, 1H), 6.68 (s, 1H), 6.10 (d, 1H), 3.62 (m, 1H), 1.80 (m, 2H), 1.64 (m, 2H), 1.52 (m, 2H), 1.29 (m, 2H), 1.16 (m, 2H).

Example 6

N-(3-(1-(6-aminopyrimidin-4-yl)-1H-indol-6-yl)phenyl)-4-chloro-3-(trifluoromethyl)benzamide

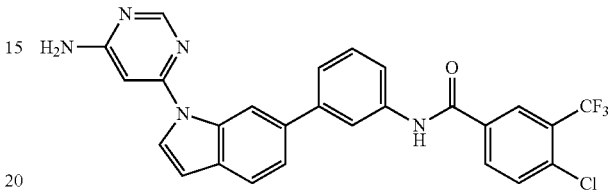

6-(6-(3-Aminophenyl)-1H-indol-1-yl)pyrimidin-4-amine (15 mg, 0.050 mmol), 4-chloro-3-(trifluoromethyl)benzoic acid (16.8 mg, 0.075 mmol) and HOBt (6.8 mg, 0.050 mmol) were dissolved in THF (1 mL). At room temperature, EDCI (28.8 mg, 0.15 mmol) was added. The reaction solution was stirred at room temperature for 15 hours and the reaction mixture was added to saturated sodium bicarbonate aqueous solution. After adding water and ethyl acetate, the aqueous layer was extracted with ethyl acetate. The combined organic layer was washed with brine, dried with anhydrous magnesium sulfate, and concentrated under reduced pressure. Purification of the residue by column chromatography (silica gel, EA:Hx=1:4→MC:MeOH=20:1) yielded the target compound.

MS m/z [M+1] 507.98; $^1$H NMR (400 MHz, DMSO-$d_6$) d 10.62 (s, 1H), 8.59 (s, 1H), 8.42 (d, 1H), 8.41 (s, 1H), 8.29 (d, 1H), 8.04 (s, 1H), 7.95 (d, 1H), 7.93 (s, 1H), 7.83 (d, 1H), 7.73 (d, 1H), 7.50 (t, 1H), 7.48 (d, 1H), 7.46 (d, 1H), 7.01 (s, 2H), 6.80 (d, 1H), 6.68 (s, 1H).

Example 7

N-(3-(1-(6-aminopyrimidin-4-yl)-1H-indol-6-yl)phenyl)-3-morpholino-5-(trifluoromethyl)benzamide

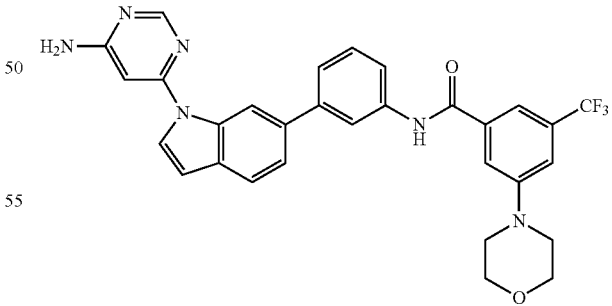

The target compound was prepared in the same manner as Example 6 using an appropriate starting material.

MS m/z [M+1] 559.10; $^1$H NMR (400 MHz, DMSO-$d_6$) d 10.46 (s, 1H), 8.60 (s, 1H), 8.47 (s, 1H), 8.04 (s, 1H), 7.95 (d, 1H), 7.88 (d, 1H), 7.75 (d, 1H), 7.73 (s, 1H), 7.69 (s, 1H), 7.51 (d, 1H), 7.49 (t, 1H), 7.47 (d, 1H), 7.40 (s, 1H), 7.06 (s, 2H), 6.80 (d, 1H), 6.68 (s, 1H), 3.77 (m, 4H), 3.37 (m, 4H).

Example 8

N-(3-(1-(6-aminopyrimidin-4-yl)-1H-indol-6-yl)phenyl)-3-(4-methyl-1H-imidazol-1-yl)-5-(trifluoromethyl)benzamide

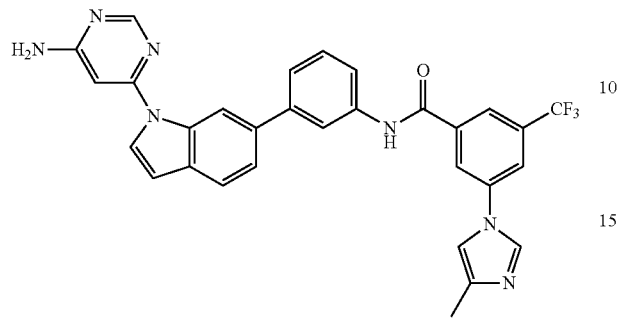

The target compound was prepared in the same manner as Example 6 using an appropriate starting material.

MS m/z [M+1] 555.07; $^1$H NMR (400 MHz, DMSO-d$_6$) d 10.62 (s, 1H), 8.61 (s, 1H), 8.49 (s, 1H), 8.42 (s, 2H), 8.26 (s, 1H), 8.21 (s, 1H), 8.01 (s, 1H), 7.95 (d, 1H), 7.85 (d, 1H), 7.76 (s, 1H), 7.73 (d, 1H), 7.54 (d, 1H), 7.50 (t, 1H), 7.47 (d, 1H), 7.06 (s, 2H), 6.80 (d, 1H), 6.68 (s, 1H), 2.19 (d, 3H).

Example 9

N-(3-(1-(6-aminopyrimidin-4-yl)-1H-indol-6-yl)phenyl)-3-(2-cyanopropan-2-yl)benzamide

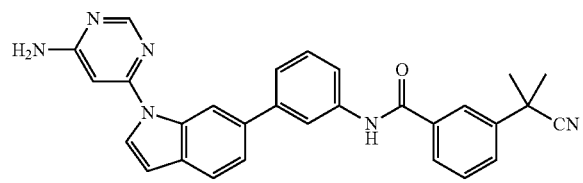 [SMILES: CC(C)(C#N)c1cccc(C(=O)Nc2cccc(-c3ccc4ccn(-c5cc(N)ncn5)c4c3)c2)c1]

The target compound was prepared in the same manner as Example 6 using an appropriate starting material.

MS m/z [M+1] 474.06; $^1$H NMR (400 MHz, DMSO-d$_6$) d 10.42 (s, 1H), 8.60 (s, 1H), 8.37 (s, 1H), 8.05 (d, 2H), 7.99 (s, 1H), 7.96 (t, 1H), 7.84 (d, 1H), 7.77 (s, 1H), 7.73 (d, 1H), 7.61 (t, 1H), 7.51 (d, 1H), 7.46 (d, 1H), 7.44 (d, 1H), 7.06 (s, 2H), 6.80 (d, 1H), 6.68 (s, 1H), 1.76 (s, 6H).

Example 10

N-(3-(1-(6-aminopyrimidin-4-yl)-1H-indol-6-yl)phenyl)-5-(4-methoxyphenyl)furan-2-carboxamide

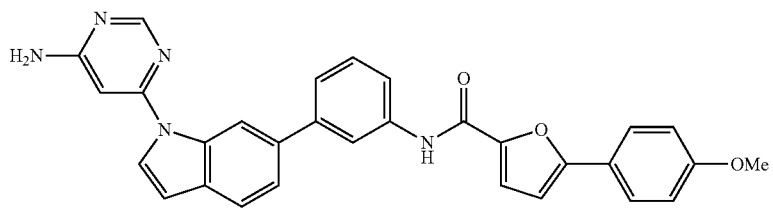 [SMILES: COc1ccc(-c2ccc(C(=O)Nc3cccc(-c4ccc5ccn(-c6cc(N)ncn6)c5c4)c3)o2)cc1]

The target compound was prepared in the same manner as Example 6 using an appropriate starting material.

MS m/z [M+1] 502.05; $^1$H NMR (400 MHz, DMSO-d$_6$) d 10.20 (s, 1H), 8.56 (s, 1H), 8.40 (s, 1H), 8.02 (s, 1H), 7.93 (d, J=3.53 Hz, 1H), 7.88 (d, J=8.72 Hz, 2H), 7.81 (d, J=7.55 Hz, 1H), 7.71 (d, J=8.17 Hz, 1H), 7.47 (t, J=2.9 Hz, 1H), 7.45 (d, J=4.66 Hz, 1H), 7.43 (d, J=4.08 Hz, 1H), 7.38 (d, J=3.62 Hz, 1H), 7.05 (s, 2H), 7.03 (d, J=8.59 Hz, 2H), 7.01 (d, J=3.40 Hz, 1H), 6.77 (d, J=3.52 Hz, 1H), 6.67 (s, 1H), 3.79 (s, 3H).

Example 11

N-(3-(1-(6-aminopyrimidin-4-yl-1H-indol-6-yl)phenyl)-5-(2-chloro-5-(trifluoromethyl)phenyl)furan-2-carboxamide

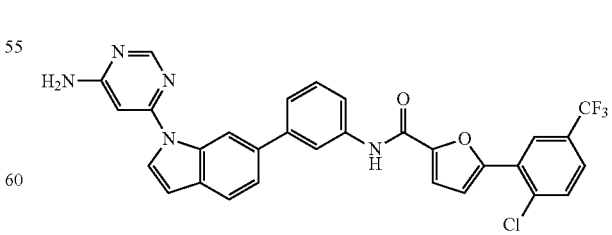

The target compound was prepared in the same manner as Example 6 using an appropriate starting material.

MS m/z [M+1] 574.00; $^1$H NMR (400 MHz, DMSO-d$_6$) d 10.49 (s, 1H), 8.63 (s, 1H), 8.50 (s, 1H), 8.42 (s, 1H), 7.95 (d,

J=3.56 Hz, 1H), 7.83 (d, J=1.82 Hz, 1H), 7.79 (d, J=2.10 Hz, 1H), 7.71 (d, J=1.76 Hz, 1H), 7.70 (d, J=3.57 Hz, 1H), 7.66 (t, J=3.33 Hz, 1H), 7.65 (d, J=5.55 Hz, 1H), 7.53 (d, J=3.74 Hz, 1H), 7.50 (s, 1H), 7.48 (d, J=2.93 Hz, 1H), 7.47 (d, J=1.52 Hz, 1H), 7.06 (s, 2H), 6.80 (d, J=3.46 Hz, 1H), 6.68 (s, 1H).

Example 12

N-(3-(1-(6-aminopyrimidin-4-yl)-1H-indol-6-yl)phenyl)-2,5-dimethylfuran-3-carboxamide

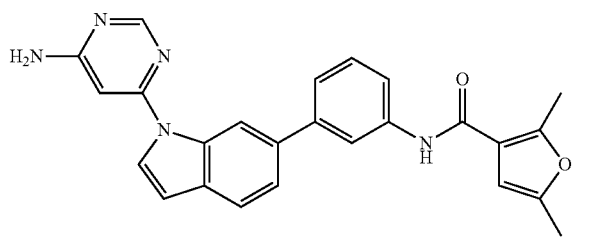 [SMILES: Cc1cc(C(=O)Nc2cccc(-c3ccc4ccn(-c5cc(N)ncn5)c4c3)c2)c(C)o1]

The target compound was prepared in the same manner as Example 6 using an appropriate starting material.

MS m/z [M+1] 424.06; $^1$H NMR (400 MHz, DMSO-$d_6$) d 9.68 (s, 1H), 8.57 (s, 1H), 8.41 (s, 1H), 8.00 (s, 1H), 7.94 (d, J=3.53 Hz, 1H), 7.78 (d, J=7.54 Hz, 1H), 7.74 (d, J=8.17 Hz, 1H), 7.46 (d, J=4.47 Hz, 1H), 7.44 (t, J=3.86 Hz, 1H), 7.40 (d, J=3.41 Hz, 1H), 7.06 (s, 2H), 6.79 (d, J=3.54 Hz, 1H), 6.70 (s, 1H), 6.68 (s, 1H), 2.51 (s, 3H), 2.27 (s, 3H).

Example 13

N-(3-(1-(6-aminopyrimidin-4-yl)-1H-indol-6-yl)phenyl)-5-methylisoxazol-3-carboxamide

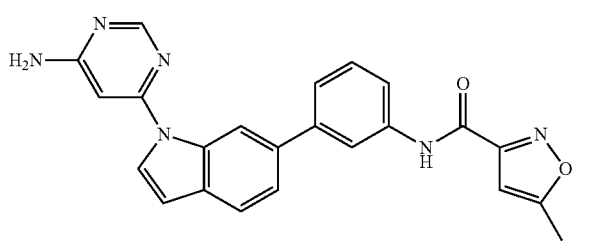 [SMILES: Cc1cc(C(=O)Nc2cccc(-c3ccc4ccn(-c5cc(N)ncn5)c4c3)c2)no1]

The target compound was prepared in the same manner as Example 6 using an appropriate starting material.

MS m/z [M+1] 411.04; $^1$H NMR (400 MHz, DMSO-$d_6$) d 10.72 (s, 1H), 8.57 (s, 1H), 8.41 (s, 1H), 8.09 (s, 1H), 7.94 (d, J=3.64 Hz, 1H), 7.84 (m, 1H), 7.72 (d, J=7.78 Hz, 1H), 7.46 (d, J=4.05 Hz, 2H), 7.44 (d, J=7.91, 1H), 7.06 (s, 2H), 6.79 (d, J=3.23 Hz, 1H), 6.68 (s, 2H), 2.08 (s, 3H).

Example 14

N-(3-(1-(6-aminopyrimidin-4-yl)-1H-indol-6-yl)phenyl)-5-(4-chlorophenyl)isoxazol-3-carboxamide

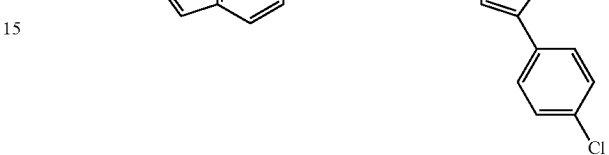

The target compound was prepared in the same manner as Example 6 using an appropriate starting material.

MS m/z [M+1] 507.02; $^1$H NMR (400 MHz, DMSO-$d_6$) d 10.88 (s, 1H), 8.59 (s, 1H), 8.42 (s, 1H), 8.11 (s, 1H), 8.01 (d, J=8.37 Hz, 2H), 7.95 (d, J=3.69 Hz, 1H), 7.86 (m, 1H), 7.73 (d, J=8.00 Hz, 1H), 7.65 (d, J=8.32 Hz, 2H), 7.58 (s, 1H), 7.48 (d, J=4.86 Hz, 2H), 7.46 (d, J=7.26 Hz, 1H), 7.06 (s, 2H), 6.80 (d, J=2.81 Hz, 1H), 6.68 (s, 1H).

Example 15

N-(3-(1-(6-aminopyrimidin-4-yl)-1H-indol-6-yl)phenyl)thiazol-4-carboxamide

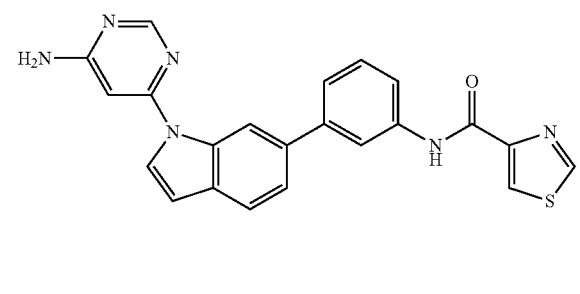 [SMILES: Nc1cc(-n2ccc3ccc(-c4cccc(NC(=O)c5cscn5)c4)cc32)ncn1]

The target compound was prepared in the same manner as Example 6 using an appropriate starting material.

MS m/z [M+1] 412.95; $^1$H NMR (400 MHz, DMSO-$d_6$) d 10.40 (s, 1H), 9.25 (s, 1H), 8.53 (s, 1H), 8.48 (d, J=1.65 Hz, 1H), 8.38 (s, 1H), 8.13 (s, 1H), 7.91 (d, J=3.53 Hz, 1H), 7.88 (dd, J=2.01, 6.62 Hz, 1H), 7.69 (d, J=8.15 Hz, 1H), 7.44 (d, J=1.32 Hz, 1H), 7.42 (s, 1H), 7.40 (t, J=6.86 Hz, 1H), 7.02 (s, 2H), 6.76 (d, J=3.52 Hz, 1H), 6.65 (s, 1H).

Example 16

N-(3-(1-(6-aminopyrimidin-4-yl)-1H-indol-6-yl)phenyl)-2-(pyridin-4-yl)thiazol-4-carboxamide

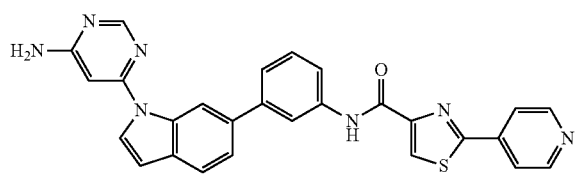 [SMILES: Nc1cc(-n2ccc3ccc(-c4cccc(NC(=O)c5csc(-c6ccncc6)n5)c4)cc32)ncn1]

The target compound was prepared in the same manner as Example 6 using an appropriate starting material.

MS m/z [M+1] 489.93; $^1$H NMR (400 MHz, DMSO-d$_6$) d 10.42 (s, 1H), 8.79 (d, J=4.50 Hz, 2H), 8.66 (s, 1H), 8.60 (s, 1H), 8.42 (s, 1H), 8.15 (d, J=3.55 Hz, 2H), 8.13 (d, J=1.56 Hz, 1H), 7.97 (d, J=3.59 Hz, 1H), 7.95 (d, J=4.00 Hz, 1H), 7.75 (d, J=8.12 Hz, 1H), 7.51 (d, J=2.44 Hz, 1H), 7.49 (s, 1H), 7.47 (m, 1H), 7.07 (s, 2H), 6.81 (d, J=3.45 Hz, 1H), 6.70 (s, 1H).

Example 17

N-(3-(1-(6-aminopyrimidin-4-yl)-1H-indol-6-yl)phenyl)-1-phenyl-5-(trifluoromethyl)-1H-pyrazol-4-carboxamide

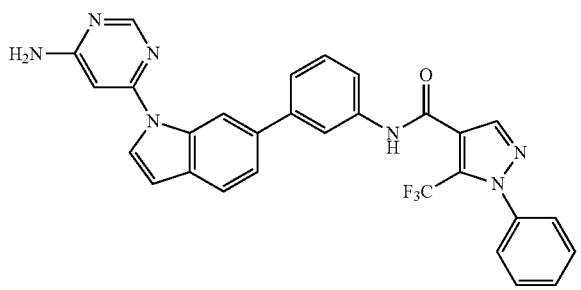 [SMILES: Nc1cc(-n2ccc3ccc(-c4cccc(NC(=O)c5cnn(-c6ccccc6)c5C(F)(F)F)c4)cc32)ncn1]

The target compound was prepared in the same manner as Example 6 using an appropriate starting material.

MS m/z [M+1] 540.00; $^1$H NMR (400 MHz, DMSO-d$_6$) d 10.63 (s, 1H), 8.60 (s, 1H), 8.41 (s, 1H), 8.34 (s, 1H), 7.98 (s, 1H), 7.95 (d, J=3.56 Hz, 1H), 7.78 (d, J=7.12 Hz, 1H), 7.54 (d, J=8.14 Hz, 1H), 7.61 (t, J=3.24 Hz, 1H), 7.58 (d, J=2.1 Hz, 1H), 7.56 (d, J=3.91 Hz, 1H), 7.53 (d, J=3.74 Hz, 1H), 7.51 (d, J=3.71 Hz, 1H), 7.46 (t, J=6.96 Hz, 3H), 7.05 (s, 2H), 6.79 (d, J=3.53 Hz, 1H), 6.67 (s, 1H).

Example 18

N-(3-(1-(6-aminopyrimidin-4-yl)-1H-indol-6-yl)phenyl)-5-bromothiophen-2-carboxamide

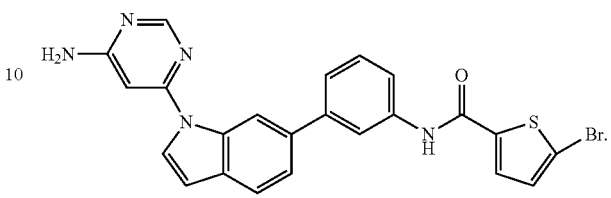

The target compound was prepared in the same manner as Example 6 using an appropriate starting material.

MS m/z [M+1] 489.80; $^1$H NMR (400 MHz, DMSO-d$_6$) d 10.39 (s, 1H), 8.58 (s, 1H), 8.42 (s, 1H), 7.98 (s, 1H), 7.96 (d, J=3.56 Hz, 1H), 7.90 (d, J=4.07 Hz, 1H), 7.78 (dd, J=1.91, 7.04 Hz, 1H), 7.73 (d, J=8.20 Hz, 1H), 7.47 (d, J=1.67 Hz, 1H), 7.45 (d, J=1.40 Hz, 1H), 7.43 (t, J=1.78 Hz, 1H), 7.39 (d, J=4.02 Hz, 1H), 7.06 (s, 2H), 6.80 (d, J=3.53 Hz, 1H), 6.68 (s, 1H).

Example 19

N-(3-(1-(6-aminopyrimidin-4-yl)-1H-indol-6-yl)phenyl)-4-(1-methylpiperidin-4-yloxy)-3-(trifluoromethyl)benzamide

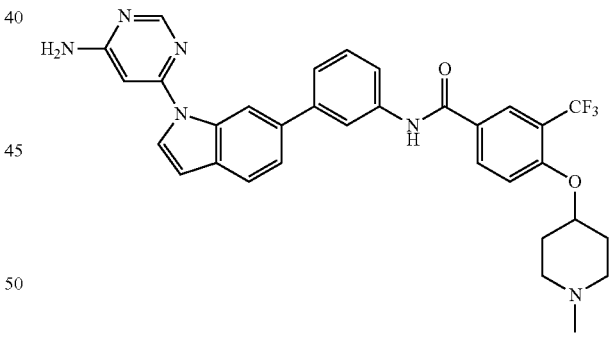

The target compound was prepared in the same manner as Example 6 using an appropriate starting material.

MS m/z [M+1] 587.11; $^1$H NMR (400 MHz, DMSO-d$_6$) d 10.40 (s, 1H), 8.59 (s, 1H), 8.41 (s, 1H), 8.27 (s, 1H), 8.25 (s, 1H), 8.04 (d, J=0.4 Hz, 2H), 7.95 (d, J=3.54 Hz, 1H), 7.84 (d, J=7.05 Hz, 1H), 7.74 (d, J=8.24 Hz, 1H), 7.48 (d, J=5.54 Hz, 2H), 7.45 (t, J=3.29 Hz, 1H), 7.06 (s, 2H), 6.80 (d, J=3.38 Hz, 1H), 6.68 (s, 1H), 3.19 (m, 1H), 2.17 (s, 3H), 1.93 (m, 4H), 1.72 (m, 4H).

Example 20

N-(3-(1-(6-aminopyrimidin-4-yl)-1H-indol-6-yl)phenyl)-4-methylbenzenesulfonamide

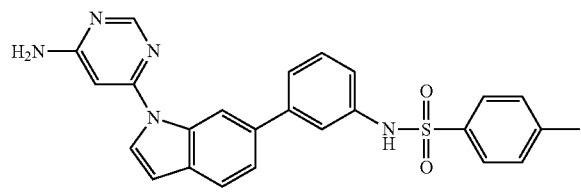 [SMILES: Cc1ccc(S(=O)(=O)Nc2cccc(-c3ccc4ccn(-c5cc(N)ncn5)c4c3)c2)cc1]

The target compound was prepared in the same manner as Example 1 using an appropriate starting material.

MS m/z [M+1] 520.00; $^1$H NMR (400 MHz, DMSO-d$_6$) d 10.52 (s, 1H), 8.52 (s, 1H), 8.46 (s, 1H), 7.96 (s, 1H), 7.94 (dd, J=1.94, 3.75 Hz, 1H), 7.82 (d, J=1.81, 7.96 Hz, 1H), 7.78 (dd, J=0.90, 7.89 Hz, 1H), 7.70 (d, J=8.16 Hz, 1H), 7.52 (t, J=7.98 Hz, 1H), 7.38 (d, J=1.98 Hz, 2H), 7.36 (s, 2H), 7.34 (d, J=1.89 Hz, 1H), 7.32 (d, J=1.51 Hz, 1H), 7.09 (dd, J=1.58, 9.09 Hz, 1H), 6.81 (d, J=3.48 Hz, 1H), 6.71 (s, 1H), 2.57 (s, 3H).

Example 21

1-(3-(1-(6-aminopyrimidin-4-yl)-1H-indol-6-yl)-4-methylphenyl)-3-(2-methoxyphenyl)urea

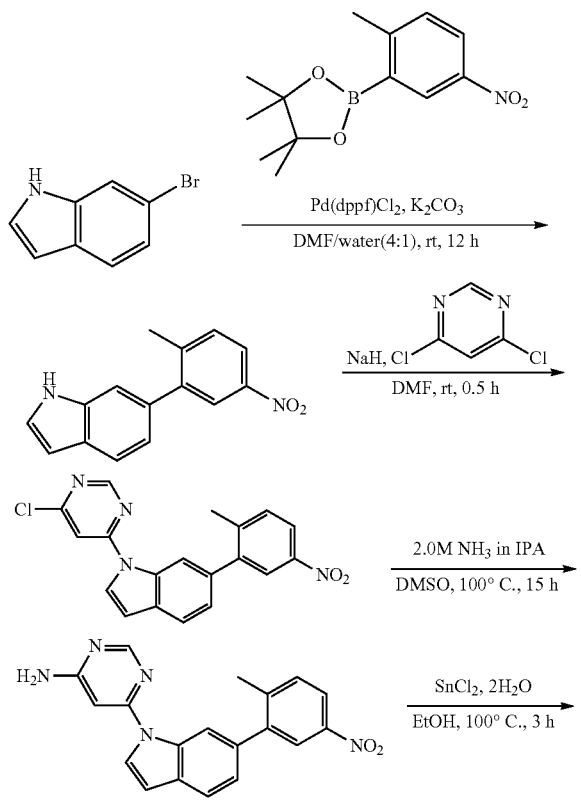

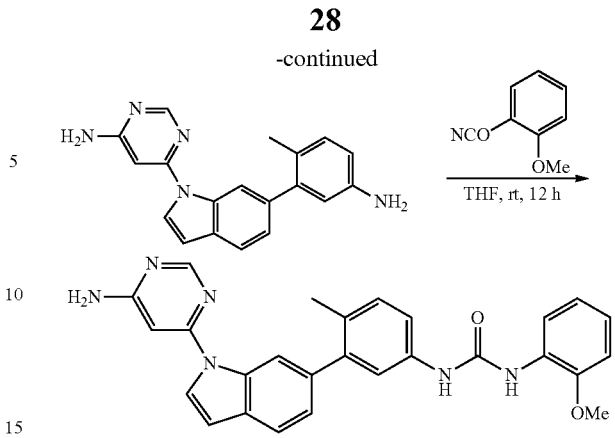

Step 1: 6-(2-methyl-5-nitrophenyl)-1H-indole

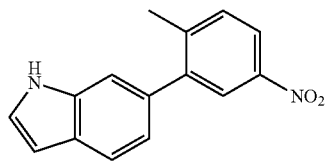 [SMILES: Cc1ccc([N+](=O)[O-])cc1-c1ccc2cc[nH]c2c1]

6-Bromo-1H-indole (203 mg, 1.04 mmol) and potassium carbonate (287 mg, 2.08 mmol) was dissolved in a DMF/water (4:1, 2.5 mL) mixture solution, and the gas included in the mixture solution was removed using ultrasonic wave and nitrogen gas. After sequentially adding 4,4,5,5-tetramethyl-2-(2-methyl-5-nitrophenyl)-1,3,2-dioxaborolane (300 mg, 1.14 mmol) and Pd(dppf)Cl$_2$ (85 mg, 0.10 mmol), the mixture was stirred at room temperature in a sealed reactor. 2 hours later, after adding ethyl acetate and water, the reaction solution was filtered through a diatomite pad. The organic layer was separated and the aqueous layer was extracted with ethyl acetate. The combined organic layer was dried with anhydrous magnesium sulfate and then concentrated. Purification of the residue by chromatography (silica gel, EA:Hx=1:4) yielded 6-(2-methyl-5-nitrophenyl)-1H-indole (170 mg) as brown solid.

MS m/z [M+1] 252.99; $^1$H NMR (400 MHz, DMSO-d$_6$) d 11.14 (NH, 1H), 8.09 (d, 1H), 8.00 (d, 1H), 7.62 (d, 1H), 7.59 (d, 1H), 7.41 (d, 1H), 7.38 (s, 1H), 6.99 (d, 1H), 6.47 (s, 1H), 2.36 (s, 3H).

Step 2: 1-(6-chloropyrimidin-4-yl)-6-(2-methyl-5-nitrophenyl)-1H-indole

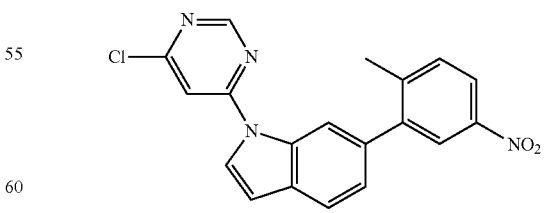

The target compound was prepared in the same manner as Step 2 of Example 1 using an appropriate starting material.

$^1$H NMR (400 MHz, DMSO-d$_6$) d 8.94 (s, 1H), 8.77 (s, 1H), 8.32 (s, 1H), 8.17 (d, 1H), 8.15 (d, 1H), 8.05 (d, 1H), 7.76 (d, 1H), 7.63 (d, 1H), 7.30 (d, 1H), 6.98 (s, 1H), 2.37 (s, 3H).

Step 3: 6-(6-(2-methyl-5-nitrophenyl)-1H-indol-1-yl)pyrimidin-4-amine

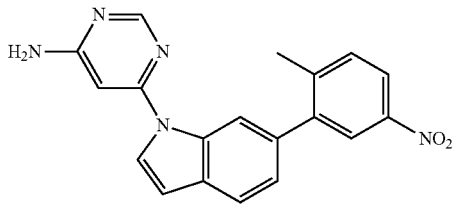

The target compound was prepared in the same manner as Step 3 of Example 1 using an appropriate starting material.
MS m/z [M+1] 346.02; $^1$H NMR (400 MHz, DMSO-d$_6$) d 8.36 (s, 1H), 8.33 (s, 1H), 8.15 (d, 1H), 8.04 (s, 1H), 8.00 (d, 1H), 7.73 (d, 1H), 7.62 (d, 1H), 7.21 (d, 1H), 7.02 (s, 2H), 6.83 (d, 1H), 6.64 (s, 1H), 2.37 (s, 3H).

Step 4: 6-(6-(5-amino-2-methylphenyl)-1H-indol-1-yl)pyrimidin-4-amine

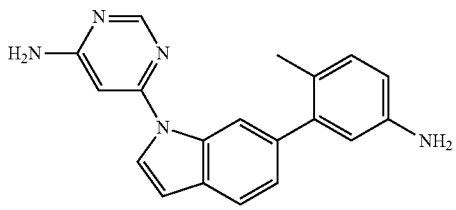 [SMILES: Cc1ccc([N+](=O)[O-])cc1-c1ccc2ccn(-c3cc(N)ncn3)c2c1]

6-(6-(2-Methyl-5-nitrophenyl)-1H-indol-1-yl)pyrimidin-4-amine (130 mg, 0.38 mmol) was dissolved in ethanol and, after adding SnCl$_2$.2H$_2$O (425 mg, 1.88 mmol), the mixture was stirred at 100° C. for 3 hours. The reaction mixture was added to sodium bicarbonate aqueous solution and extracted with ethyl acetate. The combined organic layer was washed with brine, dried with magnesium sulfate, and concentrated under reduced pressure. Purification of the residue by column chromatography (silica gel, MC:MeOH=20:1) yielded 6-(6-(5-amino-2-methylphenyl)-1H-indol-1-yl)pyrimidin-4-amine (83 mg).
MS m/z [M+1] 316.00; $^1$H NMR (400 MHz, DMSO-d$_6$) d 8.36 (s, 1H), 8.21 (s, 1H), 7.94 (d, 1H), 7.62 (d, 1H), 7.09 (d, 1H), 7.03 (s, 2H), 6.93 (d, 1H), 6.77 (d, 1H), 6.61 (s, 1H), 6.52 (s, 1H), 6.48 (d, 1H), 2.56 (s, 3H).

Step 5: 1-(3-(1-(6-aminopyrimidin-4-yl)-1H-indol-6-yl)-4-methylphenyl)-3-(2-methoxyphenyl)urea

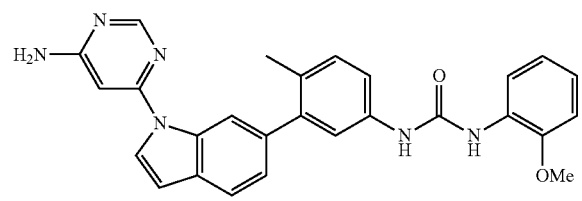 [SMILES: COc1ccccc1NC(=O)Nc1ccc(C)c(-c2ccc3ccn(-c4cc(N)ncn4)c3c2)c1]

The target compound was prepared in the same manner as Step 5 of Example 1 using an appropriate starting material.

MS m/z [M+1] 465.00; $^1$H NMR (400 MHz, DMSO-d$_6$) d 9.31 (s, 1H), 8.37 (s, 1H), 8.30 (s, 1H), 8.17 (s, 1H), 8.09 (d, 1H), 7.97 (d, 1H), 7.68 (d, 1H), 7.36 (s, 1H), 7.35 (d, 1H), 7.22 (d, 1H), 7.15 (d, 1H), 7.01 (s, 2H), 6.99 (d, 1H), 6.92 (t, 1H), 6.85 (t, 1H), 6.80 (d, 1H), 6.64 (s, 1H), 3.86 (s, 3H), 2.18 (s, 3H).

Example 22

1-(2-methoxyphenyl)-3-(3-(1-(6-(methylamino)pyrimidin-4-yl)-1H-indol-6-yl)phenyl)urea

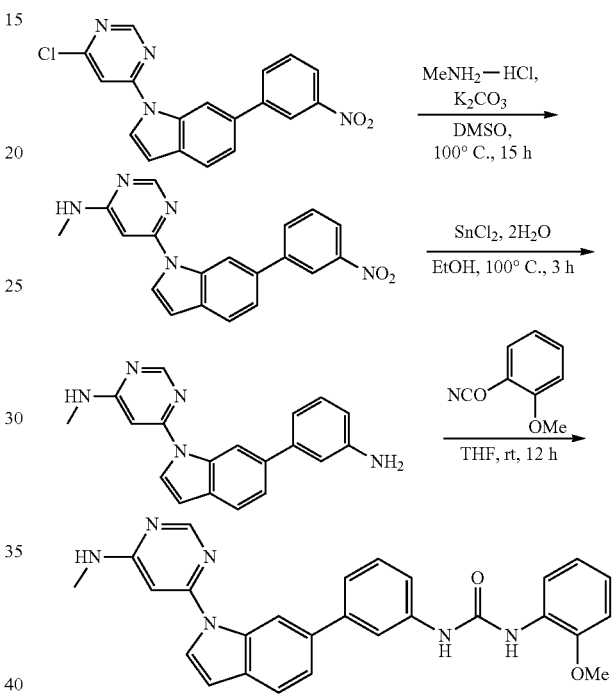

Step 1: N-methyl-6-(6-(3-nitrophenyl)-1H-indol-1-yl)pyrimidin-4-amine

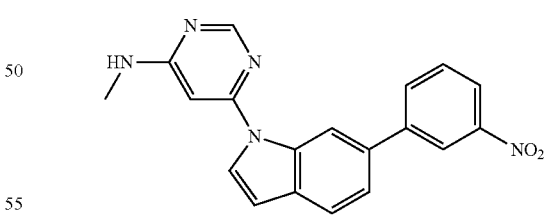

1-(6-Chloropyrimidin-4-yl)-6-(3-nitrophenyl)-1H-indole (200 mg, 0.57 mmol) and potassium carbonate (788 mg, 7.5 mmol) were dissolved in DMSO (5 mL). Methylamine hydrochloride (192 mg, 2.85 mmol) was added at room temperature. The reaction mixture was stirred at 100° C. for 15 hours. After cooling to room temperature, water was added and the reaction mixture was stirred for 1 hour. Thus prepared solid was filtered, washed with water, and dried in the air. N-Methyl-6-(6-(3-nitrophenyl)-1H-indol-1-yl)pyrimidin-4-amine (193 mg) was yielded as white solid.

MS m/z [M+1] 346.02; ¹H NMR (400 MHz, DMSO-d₆) d 8.47 (s, 1H), 8.44 (s, 1H), 8.20 (d, 1H), 8.16 (d, 2H), 7.81 (t, 1H), 7.78 (d, 1H), 7.57 (d, 1H), 7.49 (s, 1H), 6.83 (d, 1H), 6.71 (s, 1H), 2.88 (d, 3H).

Step 2: 6-(6-(3-aminophenyl)-1H-indol-1-yl)-N-methylpyrimidin-4-amine

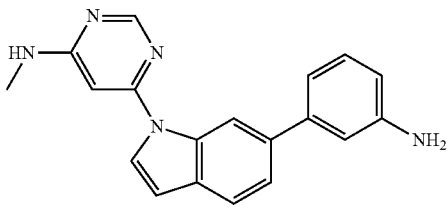 [SMILES: CNc1cc(-n2ccc3ccc(-c4cccc(N)c4)cc32)ncn1]

The target compound was prepared in the same manner as Step 4 of Example 21 using an appropriate starting material.
MS m/z [M+1] 316.09; ¹H NMR (400 MHz, DMSO-d₆) d 8.57 (s, 1H), 8.08 (s, 1H), 7.65 (d, 1H), 7.50 (s, 1H), 7.36 (d, 1H), 7.11 (t, 1H), 6.87 (d, 1H), 6.80 (d, 1H), 6.77 (d, 1H), 6.74 (s, 1H), 6.67 (s, 1H), 6.54 (d, 1H), 5.16 (s, 2H), 2.87 (d, 3H).

Step 3: 1-(2-methoxyphenyl)-3-(3-(1-(6-(methylamino)pyrimidin-4-yl)-1H-indol-6-yl)phenyl)urea

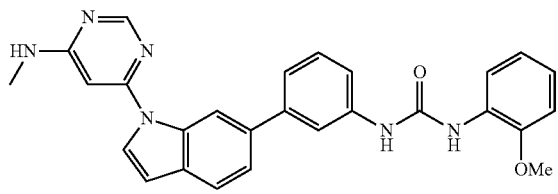 [SMILES: CNc1cc(-n2ccc3ccc(-c4cccc(NC(=O)Nc5ccccc5OC)c4)cc32)ncn1]

The target compound was prepared in the same manner as Step 5 of Example 21 using an appropriate starting material.
MS m/z [M+1] 465.05; ¹H NMR (400 MHz, DMSO-d₆) d 9.49 (s, 1H), 8.47 (s, 1H), 8.26 (s, 1H), 8.15 (d, 1H), 8.13 (d, 1H), 7.75 (s, 1H), 7.71 (d, 1H), 7.51 (s, 1H), 7.48 (s, 1H), 7.45 (d, 1H), 7.43 (d, 1H), 7.39 (t, 1H), 7.27 (d, 1H), 7.01 (d, 1H), 6.95 (t, 1H), 6.89 (t, 1H), 6.80 (d, 1H), 6.70 (s, 1H), 3.88 (s, 3H), 2.88 (d, 3H).

Example 23

1-(3-(1-(6-(cyclopropylamino)pyrimidin-4-yl)-1H-indol-6-yl)phenyl)-3-(2-methoxyphenyl)urea Step 1: N-cyclopropyl-6-(6-(3-nitrophenyl)-1H-indol-1-yl)pyrimidin-4-amine

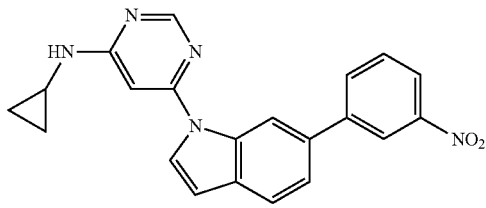

The target compound was prepared in the same manner as Step 1 of Example 22 using an appropriate starting material.
MS m/z [M+1] 372.05; ¹H NMR (400 MHz, DMSO-d₆) d 8.75 (s, 1H), 8.46 (d, 1H), 8.42 (d, 1H), 8.22 (s, 1H), 8.20 (d, 1H), 8.17 (s, 1H), 7.87 (s, 1H), 7.80 (t, 1H), 7.76 (s, 1H), 7.60 (d, 1H), 6.85 (d, 2H), 2.66 (m, 1H), 0.80 (m, 2H), 0.55 (m, 1H).

Step 2: 6-(6-(3-aminophenyl)-1H-indol-1-yl)-N-cyclopropylpyrimidin-4-amine

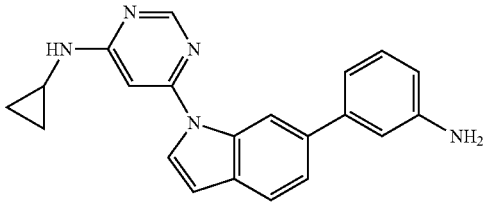 [SMILES: O=[N+]([O-])c1cccc(-c2ccc3ccn(-c4cc(NC5CC5)ncn4)c3c2)c1]

The target compound was prepared in the same manner as Step 2 of Example 22 using an appropriate starting material.
MS m/z [M+1] 342.12; ¹H NMR (400 MHz, DMSO-d₆) d 8.60 (s, 1H), 8.46 (s, 1H), 8.02 (s, 1H), 7.84 (s, 1H), 7.66 (d, 1H), 7.37 (d, 1H), 7.10 (t, 1H), 6.87 (d, 1H), 6.82 (s, 1H), 6.79 (d, 1H), 6.78 (d, 1H), 6.54 (d, 1H), 5.15 (s, 2H), 2.66 (m, 1H), 0.81 (m, 2H), 0.54 (m, 2H).

Step 3: 1-(3-(1-(6-(cyclopropylamino)pyrimidin-4-yl)-1H-indol-6-yl)phenyl)-3-(2-methoxyphenyl)urea

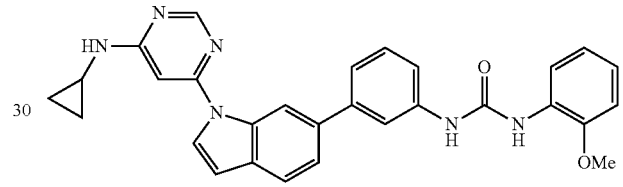

The target compound was prepared in the same manner as Step 3 of Example 22 using an appropriate starting material.
MS m/z [M+1] 491.08; ¹H NMR (400 MHz, DMSO-d₆) d 9.47 (s, 1H), 8.64 (s, 1H), 8.47 (s, 1H), 8.25 (s, 1H), 8.12 (d, 1H), 8.08 (s, 1H), 7.85 (s, 1H), 7.80 (s, 1H), 7.72 (t, 1H), 7.44 (d, 1H), 7.40 (d, 1H), 7.36 (d, 1H), 7.27 (d, 1H), 7.01 (d, 1H), 6.95 (t, 1H), 6.89 (t, 1H), 6.81 (d, 2H), 3.88 (s, 3H), 1.23 (m, 1H), 0.79 (m, 2H), 0.54 (m, 2H).

Example 24

1-(2-methoxyphenyl)-3-(3-(1-(6-(2-morpholinoethylamino)pyrimidin-4-yl)-1H-indol-6-yl)phenyl)urea Step 1: N-(2-morpholinoethyl)-6-(6-(3-nitrophenyl)-1H-indol-1-yl)pyrimidin-4-amine

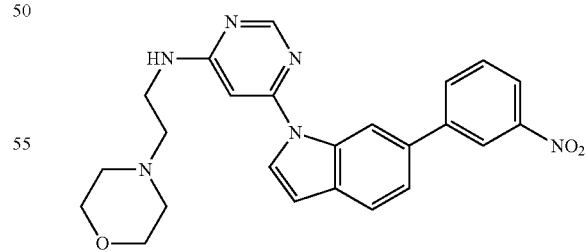

The target compound was prepared in the same manner as Step 1 of Example 22 using an appropriate starting material.
MS m/z [M+1] 445.05; ¹H NMR (400 MHz, DMSO-d₆) d 8.67 (s, 1H), 8.47 (s, 1H), 8.45 (d, 1H), 8.22 (s, 1H), 8.18 (t, 1H), 8.01 (s, 1H), 7.77 (d, 2H), 7.57 (d, 1H), 7.39 (s, 1H), 6.80 (d, 2H), 3.57 (m, 4H), 3.49 (m, 2H), 2.53 (m, 2H), 2.42 (m, 4H).

Step 2: 6-(6-(3-aminophenyl)-1H-indol-1-yl)-N-(2-morpholinoethyl)pyrimidin-4-amine

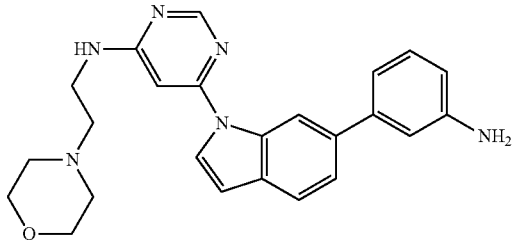 [SMILES: O=[N+]([O-])c1cccc(-c2ccc3ccn(-c4cc(NCCN5CCOCC5)ncn4)c3c2)c1]

The target compound was prepared in the same manner as Step 2 of Example 22 using an appropriate starting material.

MS m/z [M+1] 415.16; $^1$H NMR (400 MHz, DMSO-d$_6$) d 8.46 (s, 1H), 8.41 (s, 1H), 7.92 (s, 1H), 7.65 (d, 1H), 7.47 (s, 1H), 7.36 (d, 1H), 7.10 (t, 1H), 6.86 (s, 1H), 6.79 (d, 1H), 6.77 (d, 1H), 6.76 (d, 1H), 6.54 (d, 1H), 5.15 (s, 2H), 3.57 (m, 4H), 3.48 (m, 2H), 2.53 (m, 2H), 2.42 (m, 4H).

Step 3: 1-(2-methoxyphenyl)-3-(3-(1-(6-(2-morpholinoethylamino)pyrimidin-4-yl)-1H-indol-6-yl)phenyl)urea

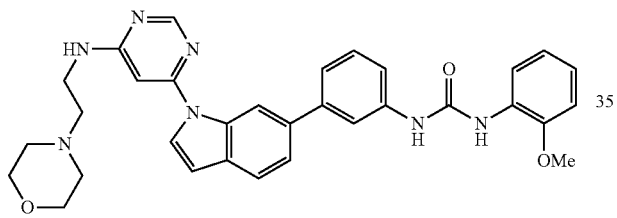

The target compound was prepared in the same manner as Step 3 of Example 22 using an appropriate starting material.

MS m/z [M+1] 564.12; $^1$H NMR (400 MHz, DMSO-d$_6$) d 9.47 (s, 1H), 8.55 (s, 1H), 8.47 (s, 1H), 8.25 (s, 1H), 8.13 (d, 1H), 7.97 (s, 1H), 7.73 (d, 1H), 7.71 (s, 1H), 7.48 (d, 1H), 7.45 (d, 1H), 7.43 (s, 1H), 7.39 (t, 1H), 7.27 (d, 1H), 7.01 (d, 1H), 6.95 (t, 1H), 6.89 (t, 1H), 6.79 (d, 2H), 3.88 (s, 3H), 3.55 (m, 4H), 4.30 (m, 2H), 2.53 (t, 2H), 2.41 (m, 4H).

Example 25

1-(3-(1-(2-aminopyrimidin-4-yl)-1H-indol-6-yl)phenyl)-3-(2-methoxyphenyl)urea

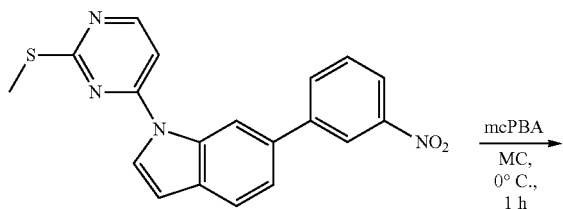

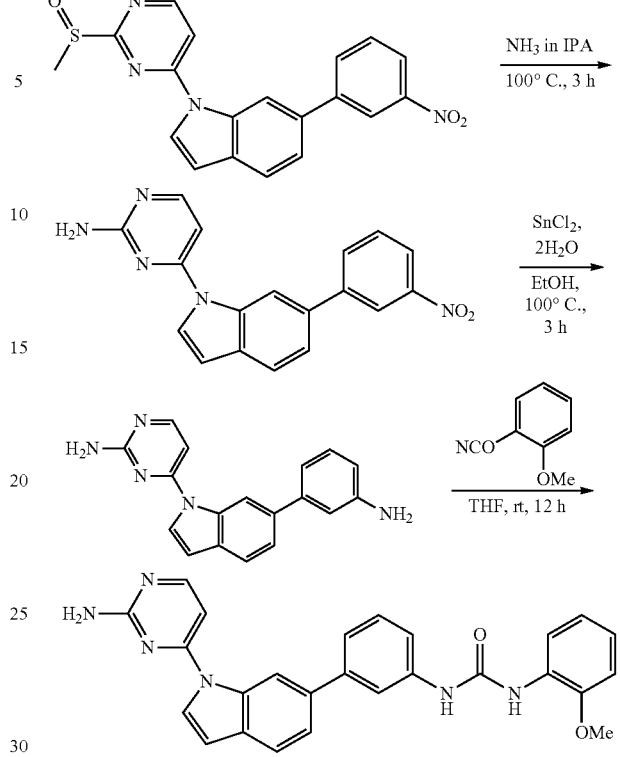

Step 1: 1-(2-(methylthio)pyrimidin-4-yl)-6-(3-nitrophenyl)-1H-indole

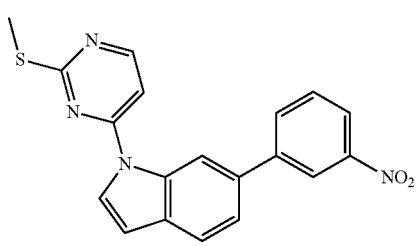 [SMILES: CSc1nccc(-n2ccc3ccc(-c4cccc([N+](=O)[O-])c4)cc32)n1]

Sodium hydride (60% in mineral oil, 40 mg, 0.98 mmol) was added at room temperature to a mixture solution of 6-(3-nitrophenyl)-1H-indole (117 mg, 0.49 mmol) in DMF (2 mL). 10 minutes later, 4-chloro-2-(methylthio)pyrimidine (68 μL, 0.59 mmol) was added. After stirring at room temperature for 30 minutes, water was added. Thus prepared solid was filtered and dried. The target compound (102 mg) was yielded as white solid.

$^1$H NMR (400 MHz, CDCl$_3$) d 8.95 (m, 1H), 8.56 (m, 1H), 8.53 (d, 1H), 8.21 (d, 1H), 8.01 (d, 1H), 7.76 (s, 1H), 7.74 (d, 1H), 7.65 (t, 1H), 7.54 (dd, 1H), 7.07 (d, 1H), 6.83 (d, 1H), 2.73 (s, 3H); MS m/z [M+1] 363.22.

Step 2: 1-(2-(methylsulfinyl)pyrimidin-4-yl)-6-(3-nitrophenyl)-1H-indole

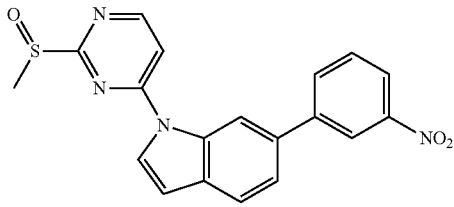 [SMILES: CS(=O)c1nccc(-n2ccc3ccc(-c4cccc([N+](=O)[O-])c4)cc32)n1]

1-(2-(Methylthio)pyrimidin-4-yl)-6-(3-nitrophenyl)-1H-indole (91 mg, 0.251 mmol) was dissolved in methylene chloride (1 mL). At 0° C., 3-chloroperoxybenzoic acid (87 mg, 0.502 mmol) was added. 1 hour later, the reaction mixture was added to sodium bicarbonate aqueous solution and extracted with methylene chloride. The combined organic layer was washed with brine, dried with magnesium sulfate, and concentrated under reduced pressure. 1-(2-(Methylsulfinyl)pyrimidin-4-yl)-6-(3-nitrophenyl)-1H-indole (102 mg) was yielded.

MS m/z [M+1] 378.96.

Step 3: 4-(6-(3-nitrophenyl)-1H-indol-1-yl)pyrimidin-2-amine

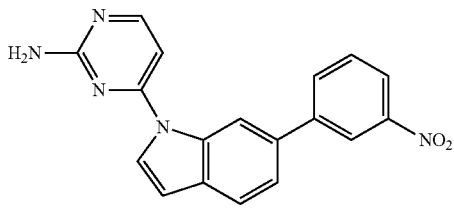

Ammonia solution (2.0 M in isopropanol) was added to 1-(2-(methylsulfinyl)pyrimidin-4-yl)-6-(3-nitrophenyl)-1H-indole (102 mg) dissolved in isopropanol. After stirring at 100° C. for 3 hours and cooling to room temperature, the reaction mixture was added to water. The aqueous layer was extracted with ethyl acetate. The combined organic layer was washed with brine, dried with magnesium sulfate, and concentrated under reduced pressure. 4-(6-(3-Nitrophenyl)-1H-indol-1-yl)pyrimidin-2-amine (76.8 mg) was yielded.

MS m/z [M+1] 331.99.

Step 4: 4-(6-(3-aminophenyl)-1H-indol-1-yl)pyrimidin-2-amine

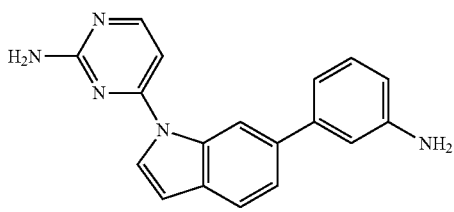 [SMILES: Nc1nccc(-n2ccc3ccc(-c4cccc([N+](=O)[O-])c4)cc32)n1]

4-(6-(3-Nitrophenyl)-1H-indol-1-yl)pyrimidin-2-amine (76.8 mg, 0.232 mmol) was dissolved in ethanol and, after adding SnCl$_2$.2H$_2$O (262 mg, 1.159 mmol), the mixture was stirred at 100° C. for 3 hours. The reaction mixture was added to sodium bicarbonate aqueous solution and extracted with ethyl acetate. The combined organic layer was washed with brine, dried with magnesium sulfate, and concentrated under reduced pressure. Purification of the residue by column chromatography (silica gel, MC:MeOH=20:1) yielded 4-(6-(3-aminophenyl)-1H-indol-1-yl)pyrimidin-2-amine (42 mg).

MS m/z [M+1] 301.98; $^1$H NMR (400 MHz, DMSO-d$_6$) d 8.82 (s, 1H), 8.28 (d, 1H), 8.02 (d, 1H), 7.63 (d, 1H), 7.41 (d, 1H), 7.08 (t, 1H), 6.98 (s, 1H), 6.95 (d, 1H), 6.90 (d, 1H), 6.87 (s, 2H), 6.77 (d, 1H), 6.54 (d, 1H).

Step 5: 1-(3-(1-(2-aminopyrimidin-4-yl)-1H-indol-6-yl)phenyl)-3-(2-methoxyphenyl)urea

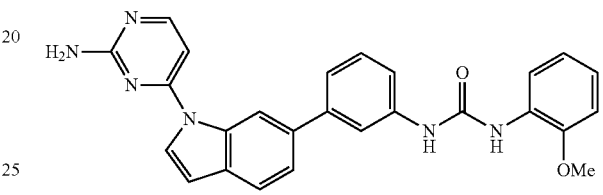

The target compound was prepared in the same manner as Example 1 using an appropriate starting material.

MS m/z [M+1] 451.01; $^1$H NMR (400 MHz, DMSO-d$_6$) d 9.46 (s, 1H), 9.01 (s, 1H), 8.29 (d, 1H), 8.27 (s, 1H), 8.14 (t, 1H), 8.07 (d, 1H), 7.91 (s, 1H), 7.68 (d, 1H), 7.48 (d, 1H), 7.39 (s, 2H), 7.02 (d, 1H), 7.00 (d, 1H), 6.98 (d, 1H), 6.94 (t, 2H), 6.88 (d, 2H), 6.79 (d, 1H), 3.88 (s, 3H).

Example 26

N-(6-(6-(3-(3-(2-methoxyphenyl)ureido)phenyl)-1H-indol-1-yl)pyrimidin-4-yl)cyclopropanecarboxamide

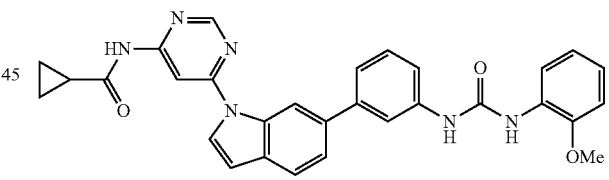

Pyridine was added to 1-(3-(1-(6-aminopyrimidin-4-yl)-1H-indol-6-yl)phenyl)-3-(2-methoxyphenyl)urea (13 mg, 0.029 mmol). At room temperature, cyclopropylcarbonyl chloride (17 μL, 0.29 mmol) was added. The reaction solution was stirred at 50° C. for 1.5 hours. After cooling to room temperature, the reaction solution was concentrated under reduced pressure. Purification of the residue by column chromatography (silica gel; EA:Hx=1:4→DCM:MeOH=20:1) yielded N-(6-(6-(3-(3-(2-methoxyphenyl)ureido)phenyl)-1H-indol-1-yl)pyrimidin-4-yl)cyclopropanecarboxamide as white solid.

MS m/z [M+1] 519.04; $^1$H NMR (400 MHz, DMSO-d$_6$) d 11.40 (s, 1H), 9.46 (s, 1H), 8.88 (s, 1H), 8.75 (s, 1H), 8.39 (s, 1H), 8.26 (s, 1H), 8.14 (d, 1H), 7.98 (d, 1H), 7.76 (d, 1H), 7.74 (s, 1H), 7.49 (t, 2H), 7.39 (t, 1H), 7.32 (d, 1H), 7.01 (d, 1H), 6.95 (d, 1H), 6.89 (d, 1H), 6.87 (d, 1H), 3.88 (s, 3H), 2.08 (m, 1H), 0.91 (t, 4H).

Example 27

N-(6-(6-(3-(3-(2-fluorophenyl)ureido)phenyl)-1H-indol-1-yl)pyrimidin-4-yl)cyclopropanecarboxamide

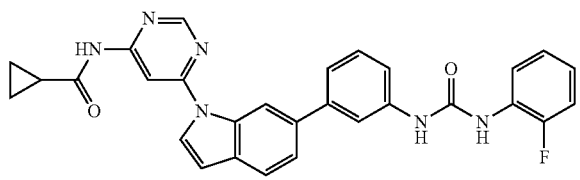 [SMILES: O=C(Nc1cccc(-c2ccc3ccn(-c4cc(NC(=O)C5CC5)ncn4)c3c2)c1)Nc1ccccc1F]

The target compound was prepared in the same manner as Example 26 using an appropriate starting material.

MS m/z [M+1] 507.12; $^1$H NMR (400 MHz, DMSO-d$_6$) d 11.40 (s, 1H), 9.21 (s, 1H), 8.81 (s, 1H), 8.75 (s, 1H), 8.58 (s, 1H), 8.40 (s, 1H), 8.17 (t, J=6.88 Hz, 1H), 7.99 (d, J=3.63 Hz, 1H), 7.78 (s, 1H), 7.76 (d, J=5.53 Hz, 1H), 7.49 (dd, J=1.35, 8.14 Hz, 1H), 7.45 (d, J=8.00 Hz, 1H), 7.40 (d, J=7.56 Hz, 1H), 7.33 (d, J=7.62 Hz, 1H), 7.24 (d, J=2.13 Hz, 1H), 7.14 (t, J=8.07 Hz, 1H), 7.02 (t, J=5.73 Hz, 1H), 6.87 (d, J=3.58 Hz, 1H), 2.08 (m, 1H), 0.90 (t, J=4.36 Hz, 4H).

Example 28

N-(6-(6-(3-(3-(3,4-dichlorophenyl)ureido)phenyl)-1H-indol-1-yl)pyrimidin-4-yl)cyclopropanecarboxamide

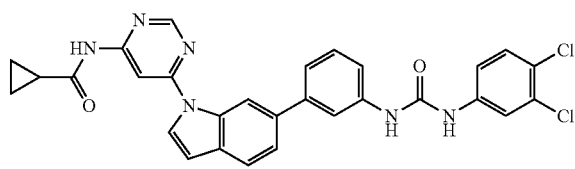 [SMILES: O=C(Nc1cccc(-c2ccc3ccn(-c4cc(NC(=O)C5CC5)ncn4)c3c2)c1)Nc1ccc(Cl)c(Cl)c1]

The target compound was prepared in the same manner as Example 26 using an appropriate starting material.

MS m/z [M+1] 557.07; $^1$H NMR (400 MHz, DMSO-d$_6$) d 11.40 (s, 1H), 9.05 (s, 1H), 8.94 (s, 1H), 8.87 (s, 1H), 8.75 (s, 1H), 8.39 (s, 1H), 7.99 (d, J=3.62 Hz, 1H), 7.90 (d, J=2.45 Hz, 1H), 7.80 (s, 1H), 7.74 (d, J=8.17 Hz, 1H), 7.51 (t, J=8.74 Hz, 1H), 7.49 (s, 1H), 7.44 (d, J=8.00 Hz, 1H), 7.40 (d, J=7.52 Hz, 1H), 7.35 (d, J=2.50 Hz, 1H), 7.33 (d, J=2.28 Hz, 1H), 6.87 (d, J=3.62 Hz, 1H), 1.48 (m, 1H), 0.89 (t, J=7.43 Hz, 4H).

Example 29

N-(6-(6-(3-(3-cyclohexylureido)phenyl)-1H-indol-1-yl)pyrimidin-4-yl)cyclopropanecarboxamide

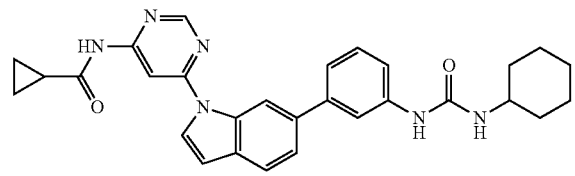 [SMILES: O=C(Nc1cccc(-c2ccc3ccn(-c4cc(NC(=O)C5CC5)ncn4)c3c2)c1)NC1CCCCC1]

The target compound was prepared in the same manner as Example 26 using an appropriate starting material.

MS m/z [M+1] 495.18; $^1$H NMR (400 MHz, DMSO-d$_6$) d 11.40 (s, 1H), 8.87 (s, 1H), 8.71 (s, 1H), 8.46 (s, 1H), 8.38 (s, 1H), 7.97 (d, J=3.64 Hz, 1H), 7.72 (d, J=8.16 Hz, 1H), 7.69 (s, 1H), 7.45 (dd, J=1.45, 8.20 Hz, 1H), 7.37 (d, J=9.17 Hz, 1H), 7.31 (t, J=7.66 Hz, 1H), 7.21 (d, J=7.68 Hz, 1H), 6.86 (d, J=3.56 Hz, 1H), 6.14 (s, 1H), 3.44 (m, 1H), 1.81 (m, 2H), 1.67 (m, 2H), 1.54 (m, 1H), 1.29 (m, 2H), 1.18 (m, 4H), 0.91 (t, J=4.32 Hz, 4H).

Example 30

4-chloro-N-(3-(1-(6-(cyclopropanecarboxamido)pyrimidin-4-yl)-1H-indol-6-yl)phenyl)-3-(trifluoromethyl)benzamide

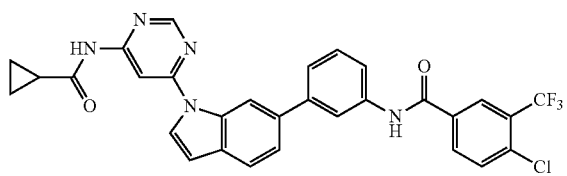 [SMILES: O=C(Nc1cccc(-c2ccc3ccn(-c4cc(NC(=O)C5CC5)ncn4)c3c2)c1)c1ccc(Cl)c(C(F)(F)F)c1]

The target compound was prepared in the same manner as Example 26 using an appropriate starting material.

MS m/z [M+1] 576.09; $^1$H NMR (400 MHz, DMSO-d$_6$) d 11.39 (s, 1H), 10.61 (s, 1H), 8.85 (s, 1H), 8.74 (s, 1H), 8.42 (d, J=1.87 Hz, 1H), 8.39 (s, 1H), 8.28 (dd, J=2.02, 8.42 Hz, 1H), 8.06 (s, 1H), 7.98 (d, J=3.62 Hz, 1H), 7.92 (d, J=8.38 Hz, 1H), 7.80 (m, 1H), 7.52 (d, J=1.43 Hz, 1H), 7.50 (d, J=1.44 Hz, 1H), 7.48 (s, 1H), 7.47 (d, J=1.75 Hz), 6.86 (d, J=3.48 Hz, 1H), 1.48 (m, 1H), 0.85 (t, J=4.8 Hz, 4H).

Example 31

N-(3-(1-(6-(cyclopropanecarboxamido)pyrimidin-4-yl)-1H-indol-6-yl)phenyl)-3-morpholino-5-(trifluoromethyl)benzamide

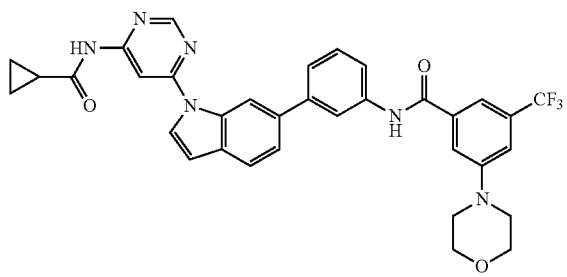 [SMILES: O=C(Nc1cccc(-c2ccc3ccn(-c4cc(NC(=O)C5CC5)ncn4)c3c2)c1)c1cc(N2CCOCC2)cc(C(F)(F)F)c1]

The target compound was prepared in the same manner as Example 26 using an appropriate starting material.

MS m/z [M+1] 627.14; $^1$H NMR (400 MHz, DMSO-d$_6$) d 11.40 (s, 1H), 10.45 (s, 1H), 8.88 (s, 1H), 8.76 (s, 1H), 8.40 (s, 1H), 8.08 (s, 1H), 8.00 (d, J=3.59 Hz, 1H), 7.81 (m, 1H), 7.78 (s, 1H), 7.76 (d, J=8.04 Hz, 1H), 7.69 (s, 1H), 7.52 (d, J=8.21 Hz, 1H), 7.48 (d, J=4.56 Hz, 1H), 7.40 (s, 1H), 6.88 (d, J=3.56 Hz, 1H), 3.78 (t, J=4.28 Hz, 4H), 2.08 (t, J=4.2 Hz, 1H), 1.22 (d, J=3.72 Hz, 2H), 0.87 (t, J=3.44 Hz, 4H), 0.83 (d, J=7.04 Hz, 2H).

Example 32

N-(3-(1-(6-(cyclopropanecarboxamido)pyrimidin-4-yl)-1H-indol-6-yl)phenyl)-3-(4-methyl-1H-imidazol-1-yl)-5-(trifluoromethyl)benzamide

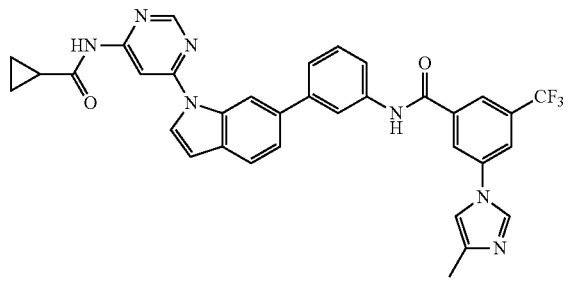 [SMILES: Cc1cn(-c2cc(C(=O)Nc3cccc(-c4ccc5ccn(-c6cc(NC(=O)C7CC7)ncn6)c5c4)c3)cc(C(F)(F)F)c2)cn1]

The target compound was prepared in the same manner as Example 26 using an appropriate starting material.

MS m/z [M+1] 622.14; ¹H NMR (400 MHz, DMSO-d₆) d 11.41 (s, 1H), 10.62 (s, 1H), 8.88 (s, 1H), 8.78 (s, 1H), 8.50 (s, 1H), 8.42 (d, J=1.34 Hz, 1H), 8.41 (s, 1H), 8.26 (s, 1H), 8.21 (s, 1H), 8.10 (s, 1H), 8.00 (d, J=3.64 Hz, 1H), 7.83 (m, 1H), 7.77 (d, J=8.16 Hz, 1H), 7.73 (s, 1H), 7.53 (d, J=1.52 Hz, 1H), 7.52 (s, 1H), 7.51 (d, J=1.52 Hz, 1H), 6.88 (d, J=3.56 Hz, 1H), 2.19 (s, 3H), 1.23 (m, 1H), 0.87 (t, J=3.5 Hz, 4H).

Example 33

3-(2-cyanopropan-2-yl)-N-(3-(1-(6-(cyclopropanecarboxamido) pyrimidin-4-yl)-1H-indol-6-yl)phenyl)benzamide

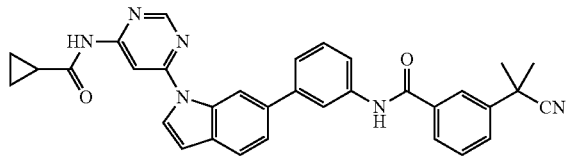 [SMILES: CC(C)(C#N)c1cccc(C(=O)Nc2cccc(-c3ccc4ccn(-c5cc(NC(=O)C6CC6)ncn5)c4c3)c2)c1]

The target compound was prepared in the same manner as Example 26 using an appropriate starting material.

MS m/z [M+1] 541.17; ¹H NMR (400 MHz, DMSO-d₆) d 11.40 (s, 1H), 10.42 (s, 1H), 8.88 (d, J=0.8 Hz, 1H), 8.78 (s, 1H), 8.40 (d, J=0.78 Hz, 1H), 8.09 (d, J=2.40 Hz, 1H), 8.08 (d, J=2.07 Hz, 1H), 7.99 (d, J=3.61 Hz, 1H), 7.98 (s, 1H), 7.82 (t, J=2.75 Hz, 1H), 7.78 (s, 1H), 7.76 (s, 1H), 7.62 (t, J=7.77 Hz, 1H), 7.53 (dd, J=1.41, 8.21 Hz, 1H), 7.49 (d, J=2.58 Hz, 1H), 7.47 (s, 1H), 1.76 (s, 6H), 1.48 (m, 1H), 0.86 (t, J=4.92 Hz, 4H).

Example 34

N-(4-(6-(3-(3-(2-methoxyphenyl)ureido)phenyl)-1H-indol-1-yl)pyrimidin-2-yl)cyclopropanecarboxamide

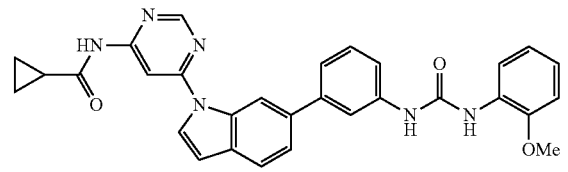 [SMILES: COc1ccccc1NC(=O)Nc1cccc(-c2ccc3ccn(-c4cc(NC(=O)C5CC5)ncn4)c3c2)c1]

The target compound was prepared in the same manner as Example 26 using an appropriate starting material.

MS m/z [M+1] 518.57; ¹H NMR (400 MHz, DMSO-d₆) d 11.40 (s, 1H), 9.46 (s, 1H), 8.88 (s, 1H), 8.75 (s, 1H), 8.39 (s, 1H), 8.26 (s, 1H), 8.14 (dd, J=1.72, 7.84 Hz, 1H), 7.98 (d, J=3.64 Hz, 1H), 7.76 (d, J=2.40 Hz, 1H), 7.74 (s, 1H), 7.49 (t, J=8.24 Hz, 2H), 7.39 (t, J=8.20 Hz, 1H), 7.32 (d, J=2.45 Hz, 1H), 7.01 (dd, J=1.44, 7.63 Hz, 1H), 6.95 (d, J=1.65 Hz, 1H), 6.93 (d, J=1.35 Hz, 1H), 6.88 (dd, J=1.48, 4.2 Hz, 1H), 3.88 (s, 3H), 2.08 (m, 1H), 0.91 (t, J=3.96 Hz, 4H).

Example 35

N-(6-(6-(5-(3-(2-methoxyphenyl)ureido)-2-methylphenyl)-1H-indol-1-yl)pyrimidin-4-yl)cyclopropanecarboxamide

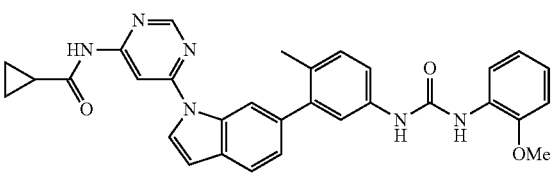 [SMILES: COc1ccccc1NC(=O)Nc1ccc(C)c(-c2ccc3ccn(-c4cc(NC(=O)C5CC5)ncn4)c3c2)c1]

The target compound was prepared in the same manner as Example 26 using an appropriate starting material.

MS m/z [M+1] 532.59; ¹H NMR (400 MHz, DMSO-d₆) d 11.36 (s, 1H), 9.31 (s, 1H), 8.82 (s, 1H), 8.49 (s, 1H), 8.32 (s, 1H), 8.17 (s, 1H), 8.09 (d, J=7.88 Hz, 1H), 7.98 (d, J=2.45 Hz, 1H), 7.70 (d, J=7.53 Hz, 1H), 7.37 (d, J=1.93 Hz, 1H), 7.37 (s, 1H), 7.22 (d, J=3.97 Hz, 1H), 7.20 (t, J=1.55 Hz, 1H), 6.99 (d, J=8.00 Hz, 1H), 6.92 (d, J=7.40 Hz, 1H), 6.89 (t, J=3.43 Hz, 1H), 6.84 (d, J=7.80 Hz, 1H), 3.86 (s, 3H), 2.20 (s, 3H), 1.47 (m, 1H), 0.88 (d, J=5.83 Hz, 4H).

Example 36

1-(3-(1-(7H-pyrrolo[2,3-d]pyrimidin-4-yl)-1H-indol-6-yl)phenyl)-3-(2-methoxyphenyl)urea Step 1: (4-chloro-7H-pyrrolo[2,3-d]pyrimidin-7-yl)methyl pivalate

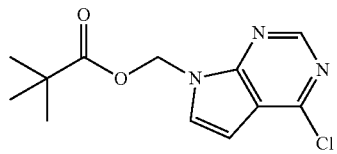 [SMILES: CC(C)(C)C(=O)OCn1ccc2c(Cl)ncnc21]

4-Chloro-7H-pyrrolo[2,3-d]pyrimidine (100 mg, 0.651 mmol) was dissolved in tetrahydrofuran (5 mL). After cooling to 0° C., the reaction mixture was added to sodium hydride (60% in mineral oil, 52 mg, 1.30 mmol). 10 minutes later, chloromethyl pivalate (0.19 mL, 1.30 mmol) was added at 0° C. After stirring for 1.5 hours at room temperature, the reaction mixture was added to saturated ammonium chloride aqueous solution. The organic layer was separated and the aqueous layer was extracted with ethyl acetate. The combined organic layer was washed with brine, dried with magnesium sulfate, and concentrated under reduced pressure. Purification of the residue by column chromatography (silica gel, EA:Hx=1:4) yielded (4-chloro-7H-pyrrolo[2,3-d]pyrimidin-7-yl)methyl pivalate (170 mg, 0.635 mmol) as white solid.

MS m/z [M+1] 268.01.

Step 2: (4-(6-(3-nitrophenyl)-1H-indol-1-yl)-7H-pyrrolo[2,3-d]pyrimidin-7-yl)methyl pivalate

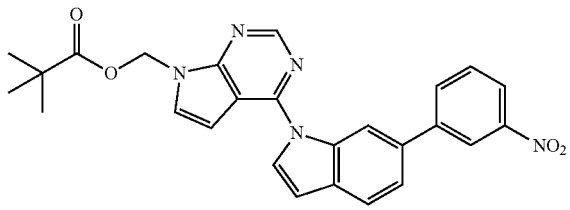

6-(3-Nitrophenyl)-1H-indole (100 mg, 0.42 mmol) and (4-chloro-7H-pyrrolo[2,3-d]pyrimidin-7-yl)methyl pivalate (112 mg, 0.42 mmol) were dissolved in 1,4-dioxane (5 mL) in a sealed reactor and then $Cs_2CO_3$ (270 mg, 0.83 mmol) was added. After removing the gas included in the solution using ultrasonic wave and sequentially adding Xantphos (CAS No. 161265-03-8; 49 mg, 0.084 mmol) and Pd(OAc)$_2$ (9.4 mg, 0.042 mmol), the reaction mixture was stirred at 120° C. for 2 hours. After cooling to room temperature and adding ethyl acetate and water, the aqueous layer was extracted with ethyl acetate. The combined organic layer was washed with brine, dried with magnesium sulfate, and concentrated under reduced pressure. Purification of the residue by column chromatography (silica gel, methylene chloride 100%) yielded (4-(6-(3-nitrophenyl)-1H-indol-1-yl)-7H-pyrrolo[2,3-d]pyrimidin-7-yl)methyl pivalate (177 mg, 0.377 mmol) as white solid.

MS m/z [M+1] 470.03; $^1$H NMR (400 MHz, DMSO-d$_6$) d 8.91 (s, 1H), 8.89 (s, 1H), 8.45 (s, 1H), 8.26 (d, J=3.53 Hz, 1H), 8.20 (d, J=8.23 Hz, 1H), 8.17 (d, J=7.30 Hz, 1H), 7.85 (d, J=7.65 Hz, 1H), 7.82 (d, J=3.62 Hz, 1H), 7.78 (t, J=7.97 Hz, 1H), 7.66 (dd, J=5.8, 6.71 Hz, 1H), 7.03 (d, J=3.79 Hz, 1H), 6.97 (d, J=3.50 Hz, 1H), 6.30 (s, 2H), 1.10 (s, 9H).

Step 3: (4-(6-(3-aminophenyl)-1H-indol-1-yl)-7H-pyrrolo[2,3-d]pyrimidin-7-yl)methyl pivalate

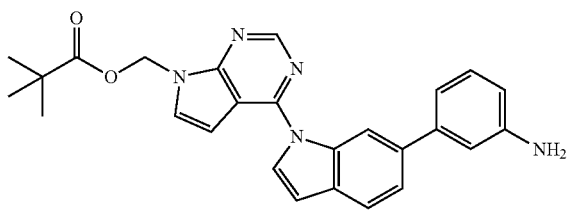 [SMILES: CC(C)(C)C(=O)OCn1ccc2c(-n3ccc4ccc(-c5cccc([N+](=O)[O-])c5)cc43)ncnc21]

(4-(6-(3-Nitrophenyl)-1H-indol-1-yl)-7H-pyrrolo[2,3-d]pyrimidin-7-yl)methyl pivalate (166 mg, 0.35 mmol) was dissolved in ethanol (5 mL). After adding tin(II) chloride dihydrate (SnCl$_2$·2H$_2$O; 80 mg, 1.75 mmol), the reaction mixture was stirred at 80° C. for 1.5 hours. After cooling to room temperature and alkalinizing the reaction mixture to pH 8 with ammonia water, ethyl acetate and sodium carbonate were added. The mixture solution was filtered through a diatomite pad and the filtrate was concentrated under reduced pressure. Purification of the residue by column chromatography (silica gel, DCM:MeOH=20:1) yielded (4-(6-(3-aminophenyl)-1H-indol-1-yl)-7H-pyrrolo[2,3-d]pyrimidin-7-yl)methyl pivalate (120 mg, 0.27 mmol) as ivory solid.

MS m/z [M+1] 440.08; $^1$H NMR (400 MHz, DMSO-d$_6$) d 8.89 (s, 1H), 8.76 (s, 1H), 8.18 (d, J=3.56 Hz, 1H), 7.81 (d, J=3.83 Hz, 1H), 7.72 (d, J=8.12 Hz, 1H), 7.44 (dd, J=1.54, 8.15 Hz), 7.10 (t, J=7.69 Hz, 1H), 7.02 (d, J=3.82 Hz, 1H), 6.92 (d, J=3.53 Hz, 1H), 6.88 (s, 1H), 6.80 (d, J=7.5 Hz, 1H), 6.54 (dd, J=2.08, 7.94 Hz, 1H), 6.29 (s, 2H), 5.16 (s, 2H), 1.10 (s, 9H).

Step 4: 1-(3-(1-(7H-pyrrolo[2,3-d]pyrimidin-4-yl)-1H-indol-6-yl)phenyl)-3-(2-methoxyphenyl)urea

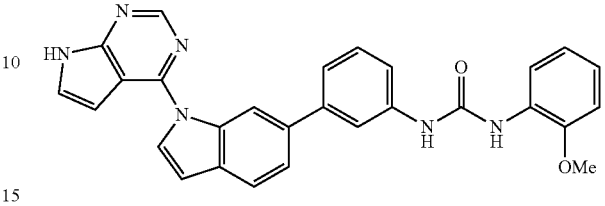

(4-(6-(3-Aminophenyl)-1H-indol-1-yl)-7H-pyrrolo[2,3-d]pyrimidin-7-yl)methyl pivalate (30 mg, 0.068 mmol) was dissolved in THF (1 mL). At room temperature, 1-isocyanato-2-methoxybenzene (32.6 μL, 0.25 mmol) was added. The reaction mixture was stirred at 50° C. for 3 hours and cooled to room temperature. After adding 1 N NaOH (1 mL) and MeOH (1 mL), the mixture solution was stirred at room temperature for 2 hours. After adding ethyl acetate and water, the organic layer was separated. The aqueous layer was extracted with ethyl acetate and the combined organic layer was washed with brine, dried with magnesium sulfate, and concentrated under reduced pressure. Purification of the residue by column chromatography (silica gel, DCM:MeOH=20:1) yielded 1-(3-(1-(7H-pyrrolo[2,3-d]pyrimidin-4-yl)-1H-indol-6-yl)phenyl)-3-(2-methoxyphenyl)urea (24.3 mg, 0.051 mmol) as white solid.

MS m/z [M+1] 475.18; $^1$H NMR (400 MHz, DMSO-d$_6$) d 9.46 (s, 1H), 8.81 (s, 1H), 8.78 (s, 1H), 8.25 (s, 1H), 8.21 (d, J=3.55 Hz, 1H), 8.15 (dd, J=1.62, 7.82 Hz, 1H), 7.79 (s, 1H), 7.77 (d, J=2.31 Hz, 1H), 7.67 (d, J=3.57 Hz, 1H), 7.49 (dd, J=1.34, 8.13 Hz, 1H), 7.44 (d, J=8.78 Hz, 1H), 7.38 (t, J=7.75 Hz, 1H), 7.27 (d, J=7.53 Hz, 1H), 7.01 (dd, J=1.35, 8.03 Hz, 1H), 6.95 (t, J=5.81 Hz, 1H), 6.92 (d, J=3.02 Hz, 1H), 6.91 (t, J=1.48 Hz, 1H), 6.89 (d, J=3.62 Hz, 1H), 3.88 (s, 3H).

Example 37

N-(3-(1-(7H-pyrrolo[2,3-d]pyrimidin-4-yl)-1H-indol-6-yl)phenyl)-4-chloro-3-(trifluoromethyl)benzamide

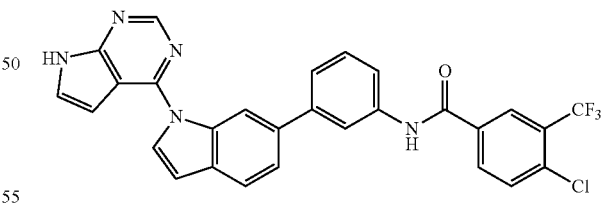

(4-(6-(3-Aminophenyl)-1H-indol-1-yl)-7H-pyrrolo[2,3-d]pyrimidin-7-yl)methyl pivalate (30 mg, 0.068 mmol), 4-chloro-3-(trifluoromethyl)benzoic acid (16.8 mg, 0.075 mmol) and HOBt (9.2 mg, 0.068 mmol) were dissolved in THF (1 mL). At room temperature, EDCI (39.2 mg, 0.20 mmol) was added. After adding 1 N NaOH (1 mL) and MeOH (1 mL), the mixture solution was stirred at room temperature for 2 hours. After adding ethyl acetate and water, the organic layer was separated. The aqueous layer was extracted with ethyl acetate and the combined organic layer was washed with brine, dried with magnesium sulfate, and concentrated under reduced pressure. Purification of the residue by column chromatography (silica gel, DCM:MeOH=20:1) yielded N-(3-(1-(7H-pyrrolo[2,3-d]pyrimidin-4-yl)-1H-indol-6-yl)phenyl)-4-chloro-3-(trifluoromethyl)benzamide (29 mg, 0.055 mmol) as white solid.

MS m/z [M+1] 532.11; $^1$H NMR (400 MHz, DMSO-$d_6$) d 8.86 (s, 1H), 8.85 (s, 1H), 8.77 (s, 1H), 8.42 (d, J=1.64 Hz, 1H), 8.29 (dd, J=2.04, 8.45 Hz, 1H), 8.22 (d, J=2.00 Hz, 1H), 8.07 (d, J=1.71 Hz, 1H), 7.95 (s, 1H), 7.93 (s, 1H), 7.81 (t, J=1.54 Hz, 1H), 7.79 (d, J=2.18 Hz, 1H), 7.67 (d, J=3.59 Hz, 1H), 7.54 (d, J=1.60 Hz, 1H), 7.52 (d, J=1.64 Hz, 1H), 7.49 (s, 1H), 6.94 (d, J=2.48 Hz, 1H), 6.89 (d, J=3.62 Hz, 1H).

The novel compound represented by Chemical Formula 1 may be prepared into various formulations depending on purposes. The following examples illustrate some formulation comprising the compound represented by Chemical Formula 1 as an active ingredient, but they do not limit the present invention.

FORMULATION EXAMPLES

Formulation Example 1

Tablet (Direct Compression)

The active ingredient (5.0 mg) was sieved, mixed with lactose (14.1 mg), crospovidone USNF (0.8 mg) and magnesium stearate (0.1 mg), and then compressed into a tablet.

Formulation Example 2

Tablet (Wet Granulation)

The active ingredient (5.0 mg) was sieved and mixed with lactose (16.0 mg) and starch (4.0 mg). An adequate amount of the resulting solution was added to Polysorbate 80 (0.3 mg) dissolved in pure water, and then formed into granules. After drying, the granules were sieved and mixed with colloidal silicon dioxide (2.7 mg) and magnesium stearate (2.0 mg). The granules were compressed into a tablet.

Formulation Example 3

Powder and Capsule

The active ingredient (5.0 mg) was sieved and mixed with lactose (14.8 mg), polyvinylpyrrolidone (10.0 mg) and magnesium stearate (0.2 mg). The mixture was filled in a hard No. 5 gelatin capsule using an adequate apparatus.

Formulation Example 4

Injection

The active ingredient (100 mg) was mixed with mannitol (180 mg), $Na_2HPO_4 \cdot 12H_2O$ (26 mg) and distilled water (2974 mg) to prepare an injection.

TEST EXAMPLES

Test Example 1

Measurement of B-Raf-V600E Kinase Activity (1) Activation of MEK1 (K97R) by B-Raf
Base reaction buffer (20 mM Hepes (pH 7.5), 10 mM $MgCl_2$, 1 mM EGTA, 0.02% Brij35, 0.02 mg/mL BSA, 0.1 mM $Na_3VO$, 2 mM DTT, 1% DMSO) was prepared. B-Raf (V600E) (Cell Signaling #7663) diluted to 30 nM was added at a final concentration of 10 nM, and MEK1 (K97R) (Upstate #14-737) diluted to 3 μM was added at a final concentration of 1 μM. The test compound was prepared at a concentration of 10 mM in dimethylsulfoxide (DMSO) and diluted to various concentrations. The final volume was adjusted to 20 μL and, after completely mixing, the mixture was allowed to react at room temperature for 30 minutes.

(2) Phosphorylation of MEK1 (K97R)
[γ-32P] ATP (100 μCi/container) diluted to ⅒ was added in 10 μL aliquots. After completely mixing, the mixture was allowed to react at room temperature for 2 hours. After placing P81 paper in a scintillation vial, spotting was performed using 30 μL of the reaction mixture. After washing 3 times with 0.75% phosphoric acid for 10 minutes and washing once with acetone for 10 minutes, 5 mL of scintillation cocktail was added to the scintillation vial holding the washed P81 paper. Signals were recorded using a scintillation counter.

The B-Raf-V600E kinase inhibition activity (% inhibition at 1 μM) of some typical compounds represented by Chemical Formula 1 is given in Table 1

TABLE 1

| Test compounds | B-Raf kinase inhibition activity (% inhibition at 1 μM) |
| --- | --- |
| Example 21 | >50 |
| Example 22 | >50 |
| Example 26 | >50 |

Test Example 2

Measurement of Inhibition Activity Against Proliferation of A375P Melanoma Cells A375P cells purchased from ATCC were cultured in DMEM [10% FBS, 1% penicillin/streptomycin] at 37° C. in the presence of 5% $CO_2$. The cultured A375P cells were harvested with 0.05% trypsin-0.02% EDTA and seeded in a 96-well plate at $5 \times 10^3$ cells per well.

3-(4,5-Dimethylthiazol-2-yl)-2,5-diphenyltetrazolium bromide (MTT) assay (CellTiter 96 Assay, Promega) was employed to measure cell viability. After adding 15 μL of a dye per well and culturing for 2 hours, the cells were treated with 100 μL of a stop solution and absorbance was measured 24 hours later. The test compound was treated a day after plating. The test compound had been sequentially diluted at 12 concentrations from a 10 mM stock solution using sterilized dimethylsulfoxide (DMSO) and treated with an amount of 0.5 μL. Absorbance at 590 nm was recorded using EnVision2103, and $GI_{50}$ value was calculated using GraphPad Prism 4.0 software.

The compounds represented by Chemical Formula 1 exhibited inhibition activity against proliferation of the A375P human melanoma cells with the B-Raf-V600E mutants overexpressed. $GI_{50}$ ranged from 0.020 to 20 μM. The inhibition activity against proliferation of the A375P cells of some typical compounds according to the present invention is given in Table 2.

TABLE 2

| Test compounds | Inhibition activity against proliferation of A375P cells (GI$_{50}$, μM) |
|---|---|
| Example 1 | <10 |
| Example 2 | <10 |
| Example 3 | <10 |
| Example 4 | <10 |
| Example 5 | <10 |
| Example 6 | <10 |
| Example 7 | <10 |
| Example 8 | <10 |
| Example 9 | <10 |
| Example 10 | <10 |
| Example 11 | <10 |
| Example 12 | <10 |
| Example 13 | <10 |
| Example 14 | <10 |
| Example 15 | <10 |
| Example 16 | <10 |
| Example 17 | <10 |
| Example 18 | <10 |
| Example 19 | <10 |
| Example 20 | <10 |
| Example 21 | <10 |
| Example 22 | <10 |
| Example 23 | <10 |
| Example 24 | <10 |
| Example 25 | <10 |
| Example 26 | <10 |
| Example 27 | <10 |
| Example 28 | <10 |
| Example 29 | <10 |
| Example 30 | <10 |
| Example 31 | <10 |
| Example 32 | <10 |
| Example 33 | <10 |
| Example 34 | <10 |
| Example 35 | <10 |
| Example 36 | <10 |
| Example 37 | <10 |

FIG. 1 shows the inhibition activity of 1-(2-methoxyphenyl)-3-(3-(1-(6-(methylamino)pyrimidin-4-yl)-1H-indol-6-yl)phenyl)urea compound (Example 22) against A375P cells at various concentrations.

Test Example 3

Measurement of Inhibition Activity Against Proliferation of SK-MEL28 Melanoma Cells SK-MEL28 cells were cultured in DMEM [10% FBS, 1% penicillin/streptomycin] at 37° C. in the presence of 5% CO$_2$. The cultured A375P cells were harvested with 0.05% trypsin-0.02% EDTA and seeded in a 96-well plate at 5×10$^3$ cells per well.

3-(4,5-Dimethylthiazol-2-yl)-2,5-diphenyltetrazolium bromide (MTT) assay (CellTiter 96 Assay, Promega) was employed to measure cell viability. After adding 15 μL of a dye per well and culturing for 2 hours, the cells were treated with 100 μL of a stop solution and absorbance was measured 24 hours later. The test compound was treated a day after plating. The test compound had been sequentially diluted at 12 concentrations from a 10 mM stock solution using sterilized dimethylsulfoxide (DMSO) and treated with an amount of 0.5 μL. Absorbance at 590 nm was recorded using EnVision2103, and GI$_{50}$ value was calculated using GraphPad Prism 4.0 software.

The compounds represented by Chemical Formula 1 exhibited inhibition activity against proliferation of the SK-MEL28 human melanoma cells with the B-Raf-V600E mutants overexpressed. GI$_{50}$ ranged from 0.070 to 10 μM.

The inhibition activity against proliferation of the SK-MEL28 cells of some typical compounds according to the present invention is given in Table 3.

TABLE 3

| Test compounds | Inhibition activity against proliferation of SK-MEL28 cells (GI$_{50}$, μM) |
|---|---|
| Example 1 | <10 |
| Example 2 | <10 |
| Example 5 | <10 |
| Example 6 | <10 |
| Example 7 | <10 |
| Example 8 | <10 |
| Example 9 | <10 |
| Example 13 | <10 |
| Example 21 | <10 |
| Example 22 | <10 |
| Example 23 | <10 |
| Example 24 | <10 |
| Example 25 | <10 |
| Example 26 | <10 |
| Example 36 | <10 |

INDUSTRIAL APPLICABILITY

As described, since the 1,6-substituted indole compound represented by Chemical Formula 1 or a pharmaceutically acceptable exhibits inhibition activity against protein kinases, it is useful for preventing and treating diseases caused by abnormal cell growth induced by protein kinases, such as cancers selected from stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma and fibroadenoma.

The present application contains subject matter related to Korean Patent Application No. 10-2009-0102359, filed in the Korean Intellectual Property Office on Oct. 27, 2009, the entire contents of which is incorporated herein by reference.

While the present invention has been described with respect to the specific embodiments, it will be apparent to those skilled in the art that various changes and modifications may be made without departing from the spirit and scope of the invention as defined in the following claims.

The invention claimed is:

1. A 1,6-substituted indole compound represented by Chemical Formula 1, a pharmaceutically acceptable salt thereof, a hydrate thereof or a solvate thereof:

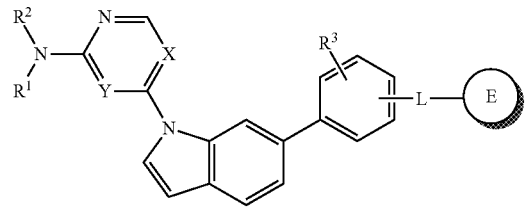

[Chemical Formula 1]

wherein

X is selected from the group consisting of N and CH;

Y is selected from the group consisting of N and $CR^a$;

L is selected from the group consisting of —$NR^4C(O)$—, —$C(O)NR^5$—, —$NR^4C(O)NR^5$— and —$NR^4S(O)_2$—;

$R^a$ is hydrogen or linked with $R^1$ to form a 5- to 7-membered ring;

$R^1$ is selected from the group consisting of hydrogen, linear, branched or cyclic $C_1$-$C_6$ alkyl, $C_1$-$C_6$ alkyl substituted with a 5- to 7-membered substituted or unsubstituted heterocycle containing 1 to 3 heteroatom(s) selected from nitrogen, oxygen and sulfur atoms, and —$C(O)R^4$;

$R^2$, $R^3$, $R^4$ and $R^5$ are independently selected from the group consisting of hydrogen and linear, branched or cyclic $C_1$-$C_6$ alkyl;

E is selected from the group consisting of linear, branched or cyclic saturated or unsaturated $C_1$-$C_6$ alkyl, 5- to 7-membered substituted or unsubstituted aryl, biaryl formed from two 5- to 7-membered substituted or unsubstituted aryls, 5- to 7-membered substituted or unsubstituted heteroaryl containing 1 to 3 heteroatom(s) selected from nitrogen, oxygen and sulfur atoms, and 5- to 7-membered substituted or unsubstituted heterocycle containing 1 to 3 heteroatom(s) selected from nitrogen, oxygen and sulfur atoms;

the aryl, heteroaryl, biaryl and heterocycle are independently substituted or unsubstituted with 1 to 3 substituent(s) selected from the group consisting of hydrogen, halogen; —CN; —$NO_2$; linear, branched or cyclic $C_1$-$C_6$ alkyl, $C_1$-$C_6$ haloalkyl containing 1 to 10 halogen atom(s), cyano $C_1$-$C_6$ alkyl, —$OR^6$, —$O(CH_2)_nNR^7R^8$ (wherein n is an integer from 1 to 6), —$NR^7R^8$, —$NR^6COR^7$, —$NR^5C(O)NR^7R^8$, —$C(O)R^7$, —$C(O)OR^7$, —$C(O)NR^7R^8$, —$C(O)NH(CH_2)_nNR^7R^8$, —$S(O)R^7$, —$S(O)_2R^7$, —$S(O)_2NR^7R^8$, 5- to 7-membered aryl, biaryl formed from two 5- to 7-membered aryls, 5- to 7-membered heteroaryl containing 1 to 3 heteroatom(s) selected from nitrogen, oxygen and sulfur atoms, and 5- to 7-membered heterocycle containing 1 to 3 heteroatom(s) selected from nitrogen, oxygen and sulfur atoms, wherein the aryl, biaryl, heteroaryl and heterocycle may be independently substituted with 1 to 3 substituent(s) selected from the group consisting of halogen, $C_1$-$C_6$ alkyl, and $C_1$-$C_6$ haloalkyl containing 1 to 10 halogen atom(s); and $R^6$, $R^7$ and $R^8$ are independently selected from the group consisting of hydrogen, halogen, linear, branched or cyclic saturated or unsaturated $C_1$-$C_6$ alkyl, 5- to 7-membered aryl, biaryl formed from two 5- to 7-membered aryls, 5- to 7-membered heteroaryl containing 1 to 3 heteroatom(s) selected from nitrogen, oxygen and sulfur atoms, and 5- to 7-membered heterocycle containing 1 to 3 heteroatom(s) selected from nitrogen, oxygen and sulfur atoms, or $R^7$ and $R^8$ of $NR^7R^8$ may form 5- to 7-membered heteroaryl or heterocycles containing a nitrogen atom or optionally, 1 to 3 other heteroatom(s), wherein the aryl, biaryl, heteroaryl and heterocycle may be independently substituted with 1 to 3 substituent(s) selected from the group consisting of halogen, $C_1$-$C_6$ alkyl, $C_1$-$C_6$ alkoxy, and $C_1$-$C_6$ haloalkyl containing 1 to 10 halogen atom(s).

2. The compound according to claim 1, wherein

X is selected from the group consisting of N and CH;

Y is selected from the group consisting of N and $CR^a$;

L is selected from the group consisting of —$NR^4C(O)$—, —$C(O)NR^5$—, —$NR^4C(O)NR^5$— and —$NR^4S(O)_2$—;

$R^a$ is hydrogen or is linked with $R^1$ to form a 5- to 7-membered ring;

$R^1$ is selected from the group consisting of hydrogen, linear, branched or cyclic $C_1$-$C_6$ alkyl, $C_1$-$C_6$ alkylmorpholino and —$C(O)R^4$;

$R^2$, $R^3$, $R^4$ and $R^5$ are independently selected from the group consisting of hydrogen and linear, branched or cyclic $C_1$-$C_6$ alkyl;

E is selected from the group consisting of linear, branched or cyclic saturated or unsaturated $C_1$-$C_6$ alkyl, substituted or unsubstituted phenyl, substituted or unsubstituted furanyl, substituted or unsubstituted oxazolyl, substituted or unsubstituted isoxazolyl, substituted or unsubstituted pyrazolyl, substituted or unsubstituted thiazolyl, and substituted or unsubstituted thiophenyl; and the substituted phenyl, furanyl, oxazolyl, isoxazolyl, pyrazolyl, thiazolyl are thiophenyl are independently substituted or unsubstituted with 1 to 3 substituent(s) selected from the group consisting of hydrogen, halogen, linear, branched or cyclic $C_1$-$C_6$ alkyl, $C_1$-$C_6$ haloalkyl containing 1 to 10 halogen atom(s), cyano $C_1$-$C_6$ alkyl, $C_1$-$C_6$ alkoxy, N—($C_1$-$C_6$ alkyl)piperidinyloxy, morpholino, substituted or unsubstituted phenyl, substituted or unsubstituted pyridinyl, and substituted or unsubstituted imidazolyl, wherein the substituted phenyl, pyridinyl or imidazolyl are independently substituted with 1 to 3 substituent(s) selected from the group consisting of halogen, $C_1$-$C_6$ alkyl, $C_1$-$C_6$ alkoxy, and $C_1$-$C_6$ haloalkyl containing 1 to 10 halogen atom(s).

3. The compound according to claim 1, wherein

X is N;

Y is selected from the group consisting of N and $CR^a$;

L is selected from the group consisting of —NHC(O)—, —NHC(O)NH— and —$NHS(O)_2$—;

$R^a$ is hydrogen or linked with $R^1$ to form a pyrrolo[2,3-d]pyrimidine ring;

$R^1$ is selected from the group consisting of hydrogen, methyl, ethyl, cyclopropyl, morpholinoethyl and —C(O)-cyclopropyl;

$R^2$ and $R^3$ are independently selected from the group consisting of hydrogen and methyl;

E is selected from the group consisting of methyl, ethyl, cyclopropyl, cyclohexyl, substituted or unsubstituted phenyl, substituted or unsubstituted furanyl, substituted or unsubstituted oxazolyl, substituted or unsubstituted isoxazolyl, substituted or unsubstituted pyrazolyl, substituted or unsubstituted thiazolyl, and substituted or unsubstituted thiophenyl; and the substituted phenyl, furanyl, oxazolyl, isoxazolyl, pyrazolyl, thiazolyl and thiophenyl are independently substituted or unsubstituted with 1 to 3 substituent(s) selected from the group consisting of hydrogen, chloro, fluoro, bromo, methyl, trifluoromethyl, cyanopropan-2-yl, methoxy, methylpiperidinyloxy, morpholino, substituted or unsubstituted phenyl, substituted or unsubstituted pyridinyl, and substituted or unsubstituted imidazolyl, wherein the substituted phenyl, pyridinyl or imidazolyl are independently substituted with 1 to 3 substituent(s) selected from the group consisting of chloro, methyl, methoxy and trifluoromethyl.

4. The compound according to claim 1, wherein

X is N;

Y is $CR^a$;

L is —NHC(O)— or —NHC(O)NH—;

R$^a$ is hydrogen or linked with R$^1$ to form a pyrrolo[2,3-d]pyrimidine ring;

R$^1$ is hydrogen, methyl, cyclopropyl, morpholinoethyl or —C(O)-cyclopropyl;

R$^2$ and R$^3$ are independently hydrogen or methyl; and

E is cyclohexyl, phenyl, 2-methoxyphenyl, 3-chloro-4-trifluorophenyl, 3-trifluoro-4-chlorophenyl, 3-morpholino-5-trifluorophenyl, 3-(4-methyl-1H-imidazol-1-yl)-5-trifluorophenyl, 3-(2-cyanopropan-2-yl)phenyl or 5-methylisoxazol-3-yl.

5. The compound according to claim 1, which is selected from the group consisting of:

1-(3-(1-(6-aminopyrimidin-4-)-1H-indol-6-yl)phenyl)-3-(2-methoxyphenyl)urea;
1-(3-(1-(6-aminopyrimidin-4-yl)-1H-indol-6-yl)phenyl)-3-(3-chloro-4-(trifluoromethyl)phenyl)urea;
1-(3-(1-(6-aminopyrimidin-4-yl)-1H-indol-6-yl)phenyl)-3-(2-fluorophenyl)urea;
1-(3-(1-(6-aminopyrimidin-4-yl)-1H-indol-6-yl)phenyl)-3-(3,4-dichlorophenyl)urea;
1-(3-(1-(6-aminopyrimidin-4-yl)-1H-indol-6-yl)phenyl)-3-cyclohexylurea;
N-(3-(1-(6-aminopyrimidin-4-yl)-1H-indol-6-yl)phenyl)-4-chloro-3-(trifluoromethyl)benzamide;
N-(3-(1-(6-aminopyrimidin-4-yl)-1H-indol-6-yl)phenyl)-3-morpholino-5-(trifluoromethyl)benzamide;
N-(3-(1-(6-aminopyrimidin-4-yl)-1H-indol-6-yl)phenyl)-3-(4-methyl-1H-imidazol-1-yl)-5-(trifluoromethyl)benzamide;
N-(3-(1-(6-aminopyrimidin-4-yl)-1H-indol-6-yl)phenyl)-3-(2-cyanopropan-2-yl)benzamide;
N-(3-(1-(6-aminopyrimidin-4-yl)-1H-indol-6-yl)phenyl)-5-(4-methoxyphenyl)furan-2-carboxamide;
N-(3-(1-(6-aminopyrimidin-4-yl-1H-indol-6-yl)phenyl)-5-(2-chloro-5-(trifluoromethyl)phenyl)furan-2-carboxamide;
N-(3-(1-(6-aminopyrimidin-4-yl)-1H-indol-6-yl)phenyl)-2,5-dimethylfuran-3-carboxamide;
N-(3-(1-(6-aminopyrimidin-4-yl)-1H-indol-6-yl)phenyl)-5-methylisoxazol-3-carboxamide;
N-(3-(1-(6-aminopyrimidin-4-yl)-1H-indol-6-yl)phenyl)-5-(4-chlorophenyl)isoxazol-3-carboxamide;
N-(3-(1-(6-aminopyrimidin-4-yl)-1H-indol-6-yl)phenyl thiazol-4-carboxamide;
N-(3-(1-(6-aminopyrimidin-4-yl)-1H-indol-6-yl)phenyl)-2-(pyridin-4-yl)thiazol-4-carboxamide;
N-(3-(1-(6-aminopyrimidin-4-yl)-1H-indol-6-yl)phenyl)-1-phenyl-5-(trifluoromethyl)-1H-pyrazol-4-carboxamide;
N-(3-(1-(6-aminopyrimidin-4-yl)-1H-indol-6-yl)phenyl)-5-bromothiophen-2-carboxamide;
N-(3-(1-(6-aminopyrimidin-4-yl)-1H-indol-6-yl)phenyl)-4-(1-methylpiperidin-4-yloxy)-3-(trifluoromethyl)benzamide;
N-(3-(1-(6-aminopyrimidin-4-yl)-1H-indol-6-yl)phenyl)-4-methylbenzenesulfonamide;
1-(3-(1-(6-aminopyrimidin-4-yl)-1H-indol-6-yl)-4-methylphenyl)-3-(2-methoxyphenyl)urea;
1-(2-methoxyphenyl)-3-(3-(1-(6-(methylamino)pyrimidin-4-yl)-1H-indol-6-yl)phenyl)urea;
1-(3-(1-(6-(cyclopropylamino)pyrimidin-4-yl)-1H-indol-6-yl)phenyl)-3-(2-methoxyphenyl)urea;
1-(2-methoxyphenyl)-3-(3-(1-(6-(2-morpholinoethylamino)pyrimidin-4-yl)-1H-indol-6-yl)phenyl)urea;
1-(3-(1-(2-aminopyrimidin-4-yl)-1H-indol-6-yl)phenyl)-3-(2-methoxyphenyl)urea;

N-(6-(6-(3-(3-(2-methoxyphenyl)ureido)phenyl)-1H-indol-1-yl)pyrimidin-4-yl)cyclopropanecarboxamide;
N-(6-(6-(3-(3-(2-fluorophenyl)ureido)phenyl)-1H-indol-1-yl)pyrimidin-4-yl)cyclopropanecarboxamide;
N-(6-(6-(3-(3-(3,4-dichlorophenyl)ureido)phenyl)-1H-indol-1-yl)pyrimidin-4-yl)cyclopropanecarboxamide;
N-(6-(6-(3-(3-cyclohexylureido)phenyl)-1H-indol-1-yl)pyrimidin-4-yl)cyclopropanecarboxamide;
4-chloro-N-(3-(1-(6-(cyclopropanecarboxamido)pyrimidin-4-yl)-1H-indol-6-yl)phenyl)-3-(trifluoromethyl)benzamide;
N-(3-(1-(6-(cyclopropanecarboxamido)pyrimidin-4-yl)-1H-indol-6-yl)phenyl)-3-morpholino-5-(trifluoromethyl)benzamide;
N-(3-(1-(6-(cyclopropanecarboxamido)pyrimidin-4-yl)-1H-indol-6-yl)phenyl)-3-(4-methyl-1H-imidazol-1-yl)-5-(trifluoromethyl)benzamide;
3-(2-cyanopropan-2-yl)-N-(3-(1-(6-(cyclopropanecarboxamido)pyrimidin-4-yl)-1H-indol-6-yl)phenyl)benzamide;
N-(4-(6-(3-(3-(2-methoxyphenyl)ureido)phenyl)-1H-indol-1-yl)pyrimidin-2-yl)cyclopropanecarboxamide;
N-(6-(6-(5-(3-(2-methoxyphenyl)ureido)-2-methylphenyl)-1H-indol-1-yl)pyrimidin-4-yl)cyclopropanecarboxamide;
1-(3-(1-(7H-pyrrolo[2,3-d]pyrimidin-4-yl)-1H-indol-6-yl)phenyl)-3-(2-methoxyphenyl)urea; and
N-(3-(1-(7H-pyrrolo[2,3-d]pyrimidin-4-yl)-1H-indol-6-yl)phenyl)-4-chloro-3-(trifluoromethyl)benzamide.

6. A pharmaceutical composition comprising the compound according to claim 1 as an effective ingredient.

7. A method for preparing a 1,6-substituted indole compound represented by Chemical Formula 1, comprising:
reducing a nitro compound represented by Chemical Formula 2 to prepare an amine compound represented by Chemical Formula 3:

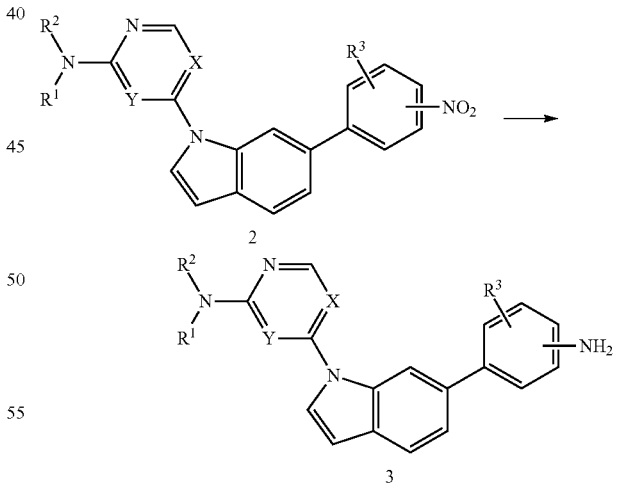

(wherein X, Y, R$^1$, R$^2$ and R$^3$ are the same as defined in claim 1); and subjecting the amine compound represented by Chemical Formula 3 to a coupling reaction with an isocyanate compound, a carboxylic acid compound, or a sulfonyl chloride compound represented by Chemical Formula 4 to prepare the compound represented by Chemical Formula 1:

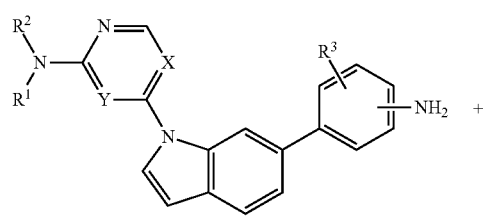
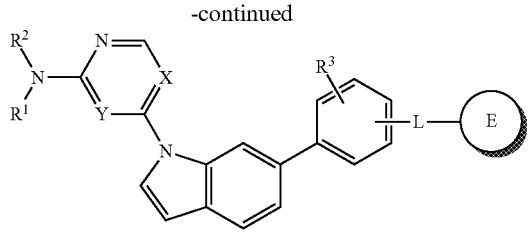
wherein X, Y, $R^1$, $R^2$, $R^3$ and E are the same as defined in claim 1, and L is selected from the group consisting of —NHC(O)NH—, —NHC(O)— and —NHS(O)$_2$—.
* * * * *